United States Patent [19]

Murray et al.

[11] Patent Number: 5,045,633

[45] Date of Patent: Sep. 3, 1991

[54] EXPRESSION OF BIOLOGICALLY ACTIVE PDGF ANALOGS IN EUCARYOTIC CELLS

[75] Inventors: Mark J. Murray; James D. Kelly, both of King County, Wash.

[73] Assignee: ZymoGenetics, Inc., Seattle, Wash.

[21] Appl. No.: 235,984

[22] Filed: Aug. 23, 1988

Related U.S. Application Data

[62] Division of Ser. No. 705,175, Feb. 25, 1985.

[51] Int. Cl.$^5$ .......................... A61K 37/36; C12N 1/22
[52] U.S. Cl. .................................... 530/399; 435/69.4
[58] Field of Search ................ 530/350, 399; 435/69.4

[56] References Cited

U.S. PATENT DOCUMENTS

| | | | |
|---|---|---|---|
| 4,350,687 | 9/1982 | Lipton et al. | 530/300 |
| 4,443,546 | 4/1984 | Stemerman et al. | 435/240 |
| 4,479,896 | 10/1984 | Antoniades | 530/380 |
| 4,546,082 | 10/1985 | Kurjan et al. | 435/172.3 |
| 4,586,640 | 2/1986 | Rubin | 435/70 |
| 4,588,585 | 5/1986 | Mark et al. | 424/85 |
| 4,590,003 | 5/1986 | Twardzik et al. | 530/330 |
| 4,599,311 | 7/1986 | Kawasaki | 435/71 |
| 4,605,413 | 8/1986 | Urry et al. | 623/011 |
| 4,645,828 | 2/1987 | Twardzik et al. | 530/324 |
| 4,673,640 | 6/1987 | Backman | 435/68 |
| 4,845,075 | 7/1989 | Murray et al. | 530/350 |

FOREIGN PATENT DOCUMENTS

| | | |
|---|---|---|
| 116201 | 10/1983 | European Pat. Off. |
| EP103409 | 3/1984 | European Pat. Off. |
| EP123294 | 10/1984 | European Pat. Off. |
| EP123544 | 10/1984 | European Pat. Off. |
| WO85/04413 | 10/1985 | PCT Int'l Appl. |
| WO86/03122 | 6/1986 | PCT Int'l Appl. |
| 2137631 | 10/1984 | United Kingdom. |
| 2146335 | 4/1985 | United Kingdom. |

OTHER PUBLICATIONS

Poggi et al., "Partial Purification and Characterization of Porcine Platelet-Derived Growth Factor (PDGF)", *Exp. Cell Res.*, 150:436–441, 1984.

Stroobant et al., "Purification and Properties of Porcine Platelet-Derived Growth Factor", *EMBO J.*, 12:2963–2967, 1984.

Wang et al., "A v-sis Oncogene Protein Produced in Bacteria Competes for Platelet-Derived Growth Factor Binding to Its Receptor", *J. Biol. Chem.*, 259:10645–10648, 1984.

Antoniades, "Platelet-Derived Growth Factor and Malignant Transformation", *Biochem. Pharm.*, 33:2823–2828, 1984.

Deuel and Huang, "Platelet-Derived Growth Factor", *J. Clin. Invest.*, 74:669–676, 1984.

Huang et al., "Transforming Protein of Simian Sarcoma Virus Stimulates Autocrine Growth of SSV-Transformed Cells Through PDGF Cell-Surface Receptors", *Cell*, 39:79–87, 1984.

Owen et al., "Simian Sarcoma Virus (SSV) Transformed Cells Secrete a Platelet-Derived Growth Factor (PDGF)-Like Mitogen", *Fed. Proc.*, 43:373, 1984.

(List continued on next page.)

Primary Examiner—Margaret Moskowitz
Assistant Examiner—Shelly J. Guest
Attorney, Agent, or Firm—Seed and Berry

[57] ABSTRACT

Biologically active PDGF analogs expressed in eucaryotic cells are disclosed. The analogs are produced by yeast strains transformed with an extrachromosomal element composed of a strong transcriptional promoter directing the expression of a gene which encodes a protein having substantially the same biological activity as PDGF. Suitable genes include the v-sis gene or a derivative of the v-sis gene of simian sarcoma virus or portions thereof, or the human cDNA gene for PDGF or portions thereof. In particular, DNA sequences encoding polypeptides substantially homologous to the B chain of PDGF are preferred. A secretory signal sequence may be provided upstream of the gene, enabling secretion of the gene product from the host cell. Mitogenic activity is one of the biological activites possessed by these PDGF analogs, making them useful in promoting the growth of mammalian cells.

7 Claims, 13 Drawing Sheets

OTHER PUBLICATIONS

Owen et al., "Simian Sarcoma Virus-Transformed Cells Secrete a Mitogen Identical to Platelet-Derived Growth Factor", *Science*, 225:54, 1984.

Robbins et al., "Structural and Immunological Similarities Between Simian Sarcoma Virus Gene Product(s) and Human Platelet-Derived Growth Factor", *Nature*, 305:605–608, 1983.

Josephs et al., "Transforming Potential of Human C-sis Nucleotide Sequences Encoding Platelet Derived Growth Factor", *Science*, 225:636–639, 1984.

Robbins et al., "Close Similarities between the Transforming Gene Product of Simian Sarcoma Virus and Human Platelet-Derived Growth Factor", *Cancer Cells*, 1:35–42, 1984.

Deuel et al., "Expression of a Platelet-Derived Growth Factor-Like Protein in Simian Sarcoma Virus Transformed Cells", *Science*, 221:1348–1350.

Raines et al., "Biologic Activity of Platelet-Derived Growth Factor-Related Sequences Expressed in Yeast", *J. Cell. Biochem. Suppl. (U.S.)*, (9A):136, (1985).

Heldin and Westermark, "Platelet-Derived Growth Factor: Mechanism of Action and Relation to Oncogenes", *Biol. Cell*, 50:11A, 1984.

Waterfield et al., "Platelet-Derived Growth Factor is Structurally Related to the Putative Transforming Protein p28sis of Simian Sarcoma Virus", *Nature*, 304:35–39, 1983.

Clarke et al., "Transformation of NIH 3T3 Cells by a Human C-sis cDNA Clone", *Nature*, 308:464, 1984.

Doolittle et al., "Simian Sarcoma Virus Onc Gene, V-sis, is Derived from the Gene (or Genes) Encoding a Platelet-Derived Growth Factor", *Science*, 221:275–277, 1983.

Dicker et al., "Similarities between Fibroblast-Derived Growth Factor and Platelet-Derived Growth Factor", *Exp. Cell Res.*, 135:221–227, 1981.

Dicker et al., "Similarities between Fibroblast-Derived Growth Factor and Platelet-Derived Growth Factor", *Chem. Abstr.*, 95:201393r, 1981.

Heldin et al., "Platelet-Derived Growth Factor", *Biochem. J.*, 193:907–913, 1981.

Robbins et al., "In Vivo Idenification of the Transforming Gene Product of Simian Sarcoma Virus", *Science*, 218:1131–1133, 1982.

Devare et al., "Nucleotide Sequence of the Simian Sarcoma Virus Genome: Demonstration that its Acquired Cellular Sequences Encode the Transforming Gene Product p28$^{sis}$", *Proc. Natl. Acad. Sci., USA*, 80:731–735, 1983.

Devare et al., "Expression of the PDGF-Related Transforming Protein of Simian Sarcoma Virus in *E. coli*", *Cell*, 36:43–49, 1984.

Deuel et al., "Human Platelet-Derived Growth Factor", *J. Biol. Chem.*, 256:8896–8899, 1981.

Johnsson et al., "The C-Sis Encodes a Precursor of the B Chain of Platelet-Derived Growth Factor", *EMBO J.*, 3:921–928, 1984.

Johnnson et al., "The C-sis Gene Encodes a Precursor of the B Chain of Platelet-Derived Growth Factor", *Chem. Abstr.*, 101:84809k, 1984.

Bourne and Rozengurt, "An 18,000 Molecular Weight Polypeptide Induces Early Events and Stimulates DNA Synthesis in Cultured Cells", *Proc. Natl. Acad. Sci. USA*, 73:4555–4559, 1976.

Waterfield et al., "Relationship between the Transforming Protein of Simian Sarcoma Virus and Human Platelet-Derived Growth Factor", *Cancer Cells*, 1:25–33, 1984.

Heldin et al., "Mechanism of Action of Platelet-Derived Growth factor and its Relation to Oncogenes", *J. Embryol. Exp. Morphol.*, 82, Suppl.: 41, 1984.

Robson et al., "Predicitions of the Conformation and Antigenic Determinants of the V-sis Viral Oncogene Product Homologous with Human Platelet-Derived Growth Factor", *Chem. Abstr.*, 102:164950k, 1985.

Johnsson et al., "Platelet-Derived Growth Factor Agonist Activity of a Secreted form of the V-sis Oncogene Product", *Proc. Natl. Acad. Sci. USA*, 82:1721–1725, 1985.

Gazit et al., "Expression of the Normal Human sis/PDGF-2 Coding Sequence Induces Cellular Transformation", *Cell*, 39:89–97, 1984.

Johnsson et al., "The Structural Relationship Between Human Platelet-Derived Growth Factor and the Transforming Protein of Simian Sarcoma Virus", *J. Cell Biochem. Suppl.*, 8A:64, 1984.

Nister et al., "A Platelet-Derived Growth Factor Analog Produced by a Human Clonal Glioma Cell Line", *Ann. N.Y. Acad. Sci.*, 397:25–33, 1982.

(List continued on next page.)

OTHER PUBLICATIONS

Rozengurt et al., "Inhibition of Epidermal Growth Factor Binding to Mouse Cultured Cells by Fibroblast-Derived Growth Factor", *J. Biol. Chem.*, 257:3680–3686, 1982.

Nister et al., "A Glioma-Derived Analog to Platelet-Derived Growth Factor: Demonstration of Receptor Competing Activity and Immunological Crossreactivity", *Proc. Natl. Acad. Sci. USA*, 81:926-9266-930, 1984.

Antoniades and Hunkapiller, "Human Platelet-Derived Growth Factor (PDGF): Amino-Terminal Amino Acid Sequence", *Science*, 220:963-965, 1983.

Antoniades, "Human Platelet-Derived Growth Factor (PDGF): Purification of PDGF-I and PDGF-II and Separation of their Reduced Subunits", *Proc. Natl. Acad. Sci. USA*, 78:7314-7317, 1981.

Johnsson et al., "Platelet-Derived Growth Factor: Identification of Constituent Polypeptide Chains", *Biochem. Biophys. Res. Comm.*, 104:66-74, 1982.

Bowen-Pope et al., "Production of Platelet-Derived Growth Factor-Like Molecules and Reduced Expression of Platelet-Derived Growth Factor Receptors Accompany Transformation by a Wide Spectrum of Agents", *Proc. Natl. Acad. Sci. USA*, 81:2396-2400, 1984.

Scher et al., "Transforming Viruses Directly Reduce the Cellular Growth Requirement for a Platelet Derived Growth Factor", *J. Cell Physiol.*, 97:371-380, 1978.

Chesterman et al., "Comparison of Platelet-Derived Growth Factor Prepared from Release Products of Fresh Platelets and from Outdated Platelet Concentrates", *Biochem. Biophys. Res. Comm.*, 116:809-816, 1983.

Westermark et al., "Platelet-Derived Growth Factor", *Horm. Cell Reg.*, 8:9-15, 1984.

Niman, "Antisera to a Synthetic Peptide of the sis Viral Oncogene Product Recognize Human Platelet-Derived Growth Factor", *Nature*, 307:180-183, 1984.

Josephs et al., "Human Proto-Oncogene Nucleotide Sequences Corresponding to the Transforming Region of Simian Sarcoma Virus", *Science*, 223:487-491, 1984.

Barth et al., "Structure and Expression of Platelet-Derived Growth Factor/c-sis Gene", *J. Cell Biochem. Suppl.*, 8A:66, 1984.

Wang et al., "Interaction of the V-SIS Gene Product with PDGF Receptor", *J. Cell Biochem. Suppl.*, 8A:258, 1984.

Goustin et al., "Expression of c-sis Oncogene and PDGF Receptors in Cell Lines Derived from Hydratidiform Mole: Implications for Autocrine Growth Control", *J. Cell Biol.*, 99(4 part 2):149a, 1984.

Hannink and Donoghue, "Requirement for a Signal Sequence in Biological Expression of the v-sis Oncogene", *Science*, 226:1197-1199, 1984.

Niman et al., "Detection of High Molecular Weight Forms of Platelet-Derived Growth Factor by Sequence-Specific Antisera," *Science* 226:701-703, 1984.

Fors et al., "Structural and Functional Studies on the Genes Encoding Platelet-Derived Growth Factor and the Platelet-Derived Growth Factor Receptor," *J. Cell Biochem.*, 0 (8 part 1):254, 1984.

Raines and Ross, "Platelet-Derived Growth Factor", *J. Biol. Chem.*, 257:5154-5160, 1982.

Raines and Ross, "Platelet Derived Growth Factor. I. High Yield Purification and Evidence for Multiple Forms", *Chem. Abstr.*, 96:213747t, 1982.

Devare et al., "Nucleotide Sequence of the Transforming Gene of Simian Sarcoma Virus", *Proc. Natl. Acad. Sci. USA*, 79:3179-3182, 1982.

Francis et al., "Chronic Myeloid Leukaemia and the Philadelphia Translocation: Do the C-CIS Oncogene and Platelet-Derived Growth Factor Provide the Link?", *Leuk. Res.*, 7:817-820, 1983.

Bowen-Pope et al., "The Ability of Cells to Synthesize and Respond to Platelet-Derived Growth Factor: Possible Involvement in Several Forms of Growth Regulation", *J. Cell Biochem. Suppl.*, 8B:94, 1984.

Chiu et al., "Nucleotide Sequence Analysis Identifies the Human c-sis Proto-Oncogene as a Structural Gene for Platelet-Derived Growth Factor", *Cell*, 37:123-129, 1984.

Antoniades et al., "Purification of Human Platelet-Derived Growth Factor", *Chem. Abstr.*, 91:15439c, 1979.

Antoniades et al., "Purification of Human Platelet-Derived Growth Factor", *Proc. Natl. Acad. Sci. USA*, 76:1809-1809-1979.

Graves et al., "Detection of c-sis Transcripts and Synthesis of PDGF-Like Proteins by Human Osteosarcoma Cells", *Science*, 226:972-974, 1984.

(List continued on next page.)

OTHER PUBLICATIONS

Heldin et al., "Chemical and Biological Properties of a Growth Factor from Human-Cultured Osteosarcoma Cells: Resemblance With Platelet-Derived Growth Factor", *J. Cell Physiol.*, 105:235-246, 1980.

Betsholtz et al., "Coexpression of a PDGF-Like Growth Factor and PDGF Receptors in a Human Osteosarcoma Cell Line: Implications for Autocrine Receptor Activation", *Cell*, 39:447-457, 1984.

Graves et al., "High Molecular Weight Precursors to Platelet-Derived Growth Factor (PDGF) are Synthesized by Human Osteosarcoma Cells", *Fed. Proc.*, 43:373, 1984.

Antoniades et al., "Purification and Properties of the Human Platelet-Derived Growth Factor", *Fed. Proc.*, 38 (3 part 1):634, 1979.

Ross et al., "The Platelet-Derived Growth Factor", *J. Supramol. Struct.* 8 (suppl. 3):175, 1979.

Wasteson et al., "Chemical and Biological Properties of Platelet Derived Growth Factor", *J. Supramol. Struct.* 9 (suppl. 4):205, 1980.

Josephs et al., "5' Viral and Human Cellular Sequences Corresponding to the Transforming Gene of Simian Sarcoma Virus", *Science* 219:503-505, 1983.

Heldin et al., "Platelet-Derived Growth Factor: Purification and Partial Characterization", *Proc. Natl. Acad. Sci., USA* 76:3722-3726, 1979.

Huang et al., "Human Platelet-Derived Growth Factor: Purification and Initial Characterization", in *Differentiation and Hematopoietic Cell Surfaces*, 225-230, 1982, Alan R. Liss, Inc., New York.

Davis and Tai, "The Mechanism of Protein Secretion Across Membranes", *Nature*, 283:433-438, 1980.

Favera et al., "A Human onc Gene Homologous to the Transforming Gene (v-sis) of Simian Sarcoma Virus", *Nature*, 292:31-35, 1981.

Wong-Staal and Gallo, "The Transforming Genes of Primate and Other Retroviruses and Their Human Homologs", *Adv. Vir. Oncol.*, 1:153-171, 1982.

Betsholtz et al., "Synthesis of a PDGF-Like Growth Factor in Human Glioma and Sarcoma Cells Suggests the Expression of the Cellular Homologue to the Transforming Protein of Simian Sarcoma Virus", *Biochem. Biophys. Res. Comm.*, 117:176-182, 1983.

Thiel and Hafenrichter, "Simian Sarcoma Virus Transformation-Specific Glycopeptide: Immunological Relationship to Human Platelet-Derived Growth Factor", *Virol.*, 136:414-424, 1984.

Seifert et al., "Developmentally Regulated Production of Platelet-Derived Growth Factor-Like Molecules", *Nature*, 311:669-671, 1984.

Rizzino and Bowen-Pope, "Production of and Response to PDGF-Like Factors by Early Embryonic Cells", *Fed. Proc.*, 43:373, 1984.

Alber and Kawasaki, "Nucleotide Sequence of the Triose Phosphate Isomerase Gene of *Saccharomyces cerevisiae*", *J. Molec. Appl. Genet.*, 1;419-434, 1982.

Kurjan et al., "Structure of a Yeast Pheromone Gene (MFa): A Putative a-Factor Precursor Contains Four Tandem Copies of Mature a-Factor", *Cell*, 30:933-943, 1982.

Brake et al., "a-Factor-Directed Synthesis and Secretion of Mature Foreign Proteins in *Saccharomyces cerevisiae*", *Proc. Natl. Acad. Sci., USA* 81:4642-4646, 1984.

Bitter et al., "Secretion of Foreign Proteins from *Saccharomyces cerevisiae* Directed by Alpha Factor Gene Fusions", *Proc. Natl. Acad. Sci., USA* 81:5330-5334, 1984.

Woo et al., "Differential Phosphorylation of the Progesterone Receptor by Insulin, Epidermal Growth Factor, and Platelet-Derived Growth Factor Receptor Tyrosine Protein Kinases", *Chem. Abstr.*, 104:45883x, 1986.

Eva et al., "Cellular Genes Analogous to Retroviral onc Genes are Transcribed in Human Tumour Cells", *Nature*, 295:116-119.

Wong-Staal et al., "The v-sis Transforming Gene of Simian Sarcoma Virus is a New onc Gene of Primate Origin", *Nature*, 294:273-275, 1981.

Edens et al., "Synthesis and Processing of the Plant Protein Thaumatin in Yeast", *Cell*, 37:629, 1984.

Wasteson et al., "The Platelet-Derived Growth Factor: Structural and Functional Aspects", *Thromb. Hemostas.*, 50(1):87, 1983.

Seifert et al., "Developmentally Regulated Production Platelet-Derived Growth Factor-Like Molecules", *J. Cell Biochem. O* (8 part 1):257, 1984.

FIG. 1A

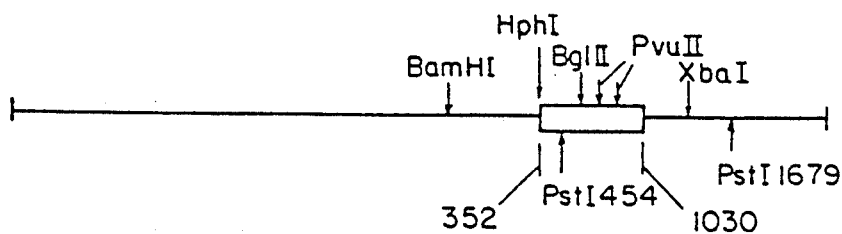

FIG. 1B

```
Hph I                    v-sis-helper viral junction
 |        367           |        382               397
CT'ATG ACC CTC ACC TGG CAG GGG GAC CCC ATT CCT GAG GAG CTC TAT AAG ATG
   MET Thr Leu Thr Trp Gln Gly Asp Pro Ile Pro Glu Glu Leu Tyr Lys MET

|Pst I
        412            427              442                 ↓  457
CTG AGT GGC CAC TCG ATT CGC TCC TTC AAT GAC CTC CAG CGC CTG CTG CAG GGA
Leu Ser Gly His Ser Ile Arg Ser Phe Asn Asp Leu Gln Arg Leu Leu Gln Gly 472              487               502
GAG TCC GGA AAA GAA GAT GGG GCT GAG CTG GAC CTG AAC ATG ACC CGC TCC CAT
Asp Ser Gly Lys Glu Asp Gly Ala Glu Leu Asp Leu Asn MET Thr Arg Ser His 517             532              547               562
TCT GGT GGC GAG CTG GAG AGC TTG GCT CGT GGG AAA AGG AGC CTG GGT TCC CTG
Ser Gly Gly Glu Leu Glu Ser Leu Ala Arg Gly Lys Arg Ser Leu Gly Ser Leu 577             592              607
AGC GTT GCC GAG CCA GCC ATG ATT GCC GAG TGC AAG ACA CGA ACC GAG GTG TTC
Ser Val Ala Glu Pro Ala MET Ile Ala Glu Cys Lys Thr Arg Thr Glu Val Phe

|Bgl II
6₂2            637              652               667
GAG ATC TCC CGG CGC CTC ATC GAC CGC ACC AAT GCC AAC TTC CTG GTG TGG CCG|
Glu Ile Ser Arg Arg Leu Ile Asp Arg Thr Asn Ala Asn Phe Leu Val Trp Pro|
```

```
                682                    697                   712                   727
 CCC TGC GTG GAG GTG CAG CGC TGC TCC GGC TGT TGC AAC AAC CGC AAC GTG CAG
 Pro Cys Val Glu Val Gln Arg Cys Ser Gly Cys Cys Asn Asn Arg Asn Val Gln

|Pvu II
                       742            |       757                   772
 TGC CGG CCC ACC CAA GTG CAG CTG CGG CCA GTC CAG GTG AGA AAG ATC GAG ATT
 Cys Arg Pro Thr Gln Val Gln Leu Arg Pro Val Gln Val Arg Lys Ile Glu Ile 787                   802                   817                   832
 GTG CGG AAG AAG CCA ATC TTT AAG AAG GCC ACG GTG ACG CTG GAG GAC CAC CTG
 Val Arg Lys Lys Pro Ile Phe Lys Lys Ala Thr Val Thr Leu Glu Asp His Leu

Pvu II
               847                    862                   877
 GCA TGC AAG TGT GAG ATA GTG GCA GCT GCA CGG GCT GTG ACC CGA AGC CCG GGG
 Ala Cys Lys Cys Glu Ile Val Ala Ala Ala Arg Ala Val Thr Arg Ser Pro Gly 892                   907                   922                   937
 ACT TCC CAG GAG CAG CGA GCC AAA ACG ACC CAA AGT CGG GTG ACC ATC CGG ACG
 Thr Ser Gln Glu Gln Arg Ala Lys Thr Thr Gln Ser Arg Val Thr Ile Arg Thr 952                   967                   982                   997
 GTG CGA GTC CGC CGG CCC CCC AAG GGC AAG CAC CGG AAA TGC AAG CAC ACG CAT
 Val Arg Val Arg Arg Pro Pro Lys Gly Lys His Arg Lys Cys Lys His Thr His 1012                  1027              1043      1053
 GAC AAG ACG GCA CTG AAG GAG ACC CTC GGA GCC TAA GGGCATCGGC AGGAGAATAT
 Asp Lys Thr Ala Leu Lys Glu Thr Leu Gly Ala 1063       1073       1083       1093       1103       1113       1123
     GGGCAGCGGG TCTCCTGCCA GCGGCCTCCA GCATCTTGCC CAGCAGCTCA AGAAGAGAAA AAAGGACTGA 1133       1143       1153       1163       1173       1183       1193
     ACTCCACCAC CATCTTCTTC CCTTAACTCC AAAAACTTGA AATAAGAGTG TGAAAGAGAC TGATAGGGTC 1203       1213       1223       1233       1243       1253       1263
     GCTGTTTGAA AAAAACTGGC TCCTTCCTCT GCACCTGGCC TGGGCCACAC CCAAGTGCTG TGGACTGGCC 1273       1283       1293       1303       1313       1323       1333
     CGAGGGGCCC TGCACGTGGC CCTGAGCACC TCTCAGTGTA GCCTGCCTGG TCCCTAGACC CCTGGCCAGC

XbaI| v-sis-helper viral junction
        1343       1353       1363       1373           ||
     TCCAAGGGGA GGCACCTCCA GGCAGGCCAG GCTACCTCGG GGGTCTAG
```

FIG. 1B CONT.

EXPRESSION OF BIOLOGICALLY ACTIVE PDGF ANALOGS IN EUCARYOTIC CELLS

CROSS REFERENCE TO RELATED APPLICATION

This application is a division of U.S. Pat. application Ser. No. 705,175, filed Feb. 25, 1985, which pending application has been allowed. Technical Field The present invention relates to the production of PDGF analogs in general, and more specifically, to the expression of biologically active PDGF analogs in eucaryotes.

BACKGROUND ART

Human platelet derived growth factor (PDGF) has been shown to be the major mitogenic protein in serum for mesenchymal derived cells. This is well documented by numerous studies of platelet extracts or purified PDGF induction of either cell multiplication or DNA synthesis (a prerequisite for cell division) in cultured smooth muscle cells, fibroblasts and glial cells (Ross et al., *PNAS* 71: 1207, 1974; Kohler and Lipton, *Exp. Cell Res.* 87: 297,1947; Westermark and Wasteson, *Exp. Cell Res.* 98: 170, 1976; Heldin et al., *J. Cell Phyiol.* 105: 235, 1980; Raines and Ross, *J. Biol. Chem* 257: 5154, 1982). Furthermore, PDGF is a potent chemoattractant for cells that are responsive to it as a mitogen (Grotendorst et al., *J. Cell Phyiol.* 113: 261, 1982; Seppa et al., *J. Cell Biol.* 92: 584, 1982). It is not generally the case that mitogens also act as chemotactic agents. Due to its mitogenic activity, PDGF is useful as an important component of a defined medium for the growth of mammalian cells in culture, making it a valuable research reagent with multiple applications in the study of animal cell biology.

In vivo, PDG( normally circulates stored in the alpha granules of platelets. Injury to arterial endothelial linings causes platelets too adhere to the exposed connective tissue and release their granules. The released PDGF is thought to chemotactically attract fibroblasts and smooth muscle cells to the site of injury and to induce their focal proliferation as part of the process of wound repair (Ross and Glomset, *N. England Journal of Medicine* 295: 369, 1976).

It has been postulated that as a part of this response to injury, PDGF released by platelets may play a causative role in the development of the proliferative lesions of atherosclerosis (Ross and Glomset, ibid.) which is one of the principal causes of myocardial and cerebral infarction. Strategies for the prophylaxis and treatment of atherogenesis in the past have been narrowly directed toward reducing risk factors for the disease, such as lowering blood pressure in hypertensive subjects and reducing elevated cholesterol levels in hypercholesterolemic subjects.

Recent studies have shown that one of the two protein chains comprising PDGF and the putative transforming protein of simian sarcoma virus (SSV), an acute transforming retrovirus, appear to have arisen from the same or closely related cellular genes. In particular, computer analysis of a partial amino acid sequence of PDGF has revealed extensive homology with the gene product, $p28^{sis}$ of SSV (Doolittle, Waterfield and Johnson, ibid.). Further, more recent studies have illustrated that p28sis and PDGF show antigenic as well as structural similarities (Robbins et al., *Nature* 305: 605, 1983; Niman, *Nature* 307: 180, 1984).

Although previous attempts, such as that summarized in Devare et al., (*Cell* 36: 43, 1984), have been made to express the v-sis gene in a transformed microorganism, they have not been successful in producing mitogenic material. More recently, investigators have described the production of $p28^{sis}$ in *E. coli* as a fusion protein. (Wang et al., *J. Biol. Chem* 259: 10645, 1984). This protein appears to compete with PDGF for binding to PDGF receptor sites. While SSV transformed rodent cells have been shown to exhibit a mitogenic activity similar to PDGF (Deuel, et al., *Science* 221: 1348, 1983; Owen, et al., *Science* 225: 54, 1984), it is not clear that this activity is due to a gene product from SSV (i.e., $p28^{sis}$). Furthermore, cells transformed by a variety of viruses other than SSV produce a PDGF-like mitogen into the culture medium (Bowen-Pope et al., *PNAS* 81: 2396, 1984).

While natural PDGF may be isolated from human plasma or platelets as starting material, it is a complex and expensive process, in part due to the limited availability of the starting material. In addition, it is difficult to purify PDGF with high yield from other serum components due to its extremely low abundance and biochemical properties. Furthermore, the therapeutic use of products derived from human blood carries the risk of disease transmission due to contamination by, for example, hepatitis virus, cytomegalovirus, or the causative agent of Acquired Immune Deficiency Syndrome (AIDS).

In view of PDGF's clinical applicability in the treatment of injuries in which healing requires the proliferation of fibroblasts or smooth muscle cells and its value as an important component of a defined medium for the growth of mammalian cells in culture, the production of useful quantities of protein molecules similar to authentic PDGF which possess mitogenic activity is clearly invaluable.

In addition, the ability to produce relatively large amounts of PDGF would be a useful tool for elucidating the putative role of the v-sis protein, $p28^{sis}$. in the neoplastic process.

Further, since local accumulation of smooth muscle cells in the intamal layer of an arterial wall is central to the development of atherosclerotic lesions (Ross and Glomset, ibid.), one strategy for the prophylaxis and treatment of atherosclerosis would be to suppress smooth muscle cell proliferation. The ability to produce large amounts of PDG( would be useful in developing inhibitors or designing specific approaches which prevent or interfere with the in vivo activity oi PDGB in individuals with atherosclerosis.

DISCLOSURE OF THE INVENTION

Briefly stated, the present invention discloses a DNA construct capable of directing the expression and secretion of biologically active PDGF analogs in eucaryotic cells. The DNA construct contains a transcriptional promoter followed downstream by a gene encoding a protein having substantially the same structure and/or mitogenic activity as PDGF, and a signal sequence capable of directing the secretion of the protein from the eucaryotic cell. The gene may be the v-sis gene or a derivative of the v-sis gene of simian sarcoma virus or portions thereof which encode a protein having biological activity. Further, the derivative of the v-sis gene may be the portion of v-sis gene which is substantially homologous to the B chain of PDGF. In addition, the gene may be the human cDNA gene for PDGF or portions thereof encoding a protein having biological activity.

Another aspect of the invention discloses a method of preparing biologically active PDGF analogs by introducing into a eucaryotic host a DNA construct capable of directing the expression and secretion of biologically active PDGF analogs in eucaryotic cells. The DNA construct contains a transcriptional promoter followed downstream by a gene encoding a protein having substantially the same structure and/or mitogenic activity as PDGF and a signal sequence capable of directing the secretion of the protein from the eucaryotic cell. Subsequent to introducing the DNA construct into the eucaryotic host, the method includes growing the eucaryotic host in an appropriate medium and then isolating the protein product of the gene from the eucaryotic host. Eucaryotic host cells transformed with such a DNA construct are also disclosed.

The present invention further provides a method for promoting the growth of mammalian cells through incubating the cells with a biologically active PDGF analog expressed by a eucaryotic cell transformed with a DNA construct capable of directing the expression and secretion of biologically active PDGF analogs in eucaryotic cells. The DNA construct contains a transcriptional promoter followed downstream by a gene encoding a protein having substantially the same structure and/or mitogenic activity as PDGF and a signal sequence capable of directing the secretion of the protein from the eucaryotic cell.

In one embodiment of the invention, the eucaryotic cell may be a yeast cell, and the DNA construct more appropriately termed an extrachromosomal element.

Other aspects of the invention will become evident upon reference to the following detailed description and attached drawings.

BRIEF DESCRIPTION OF THE DRAWINGS

FIG. 1A is a schematic restriction map of the proviral genome of SSV.

FIG. 1B depicts the nucleotide sequence and predicted amino acid sequence encoded by the v-sis region of SSV genome.

BEST MODE FOR CARRYING OUT THE INVENTION

Figure 2:
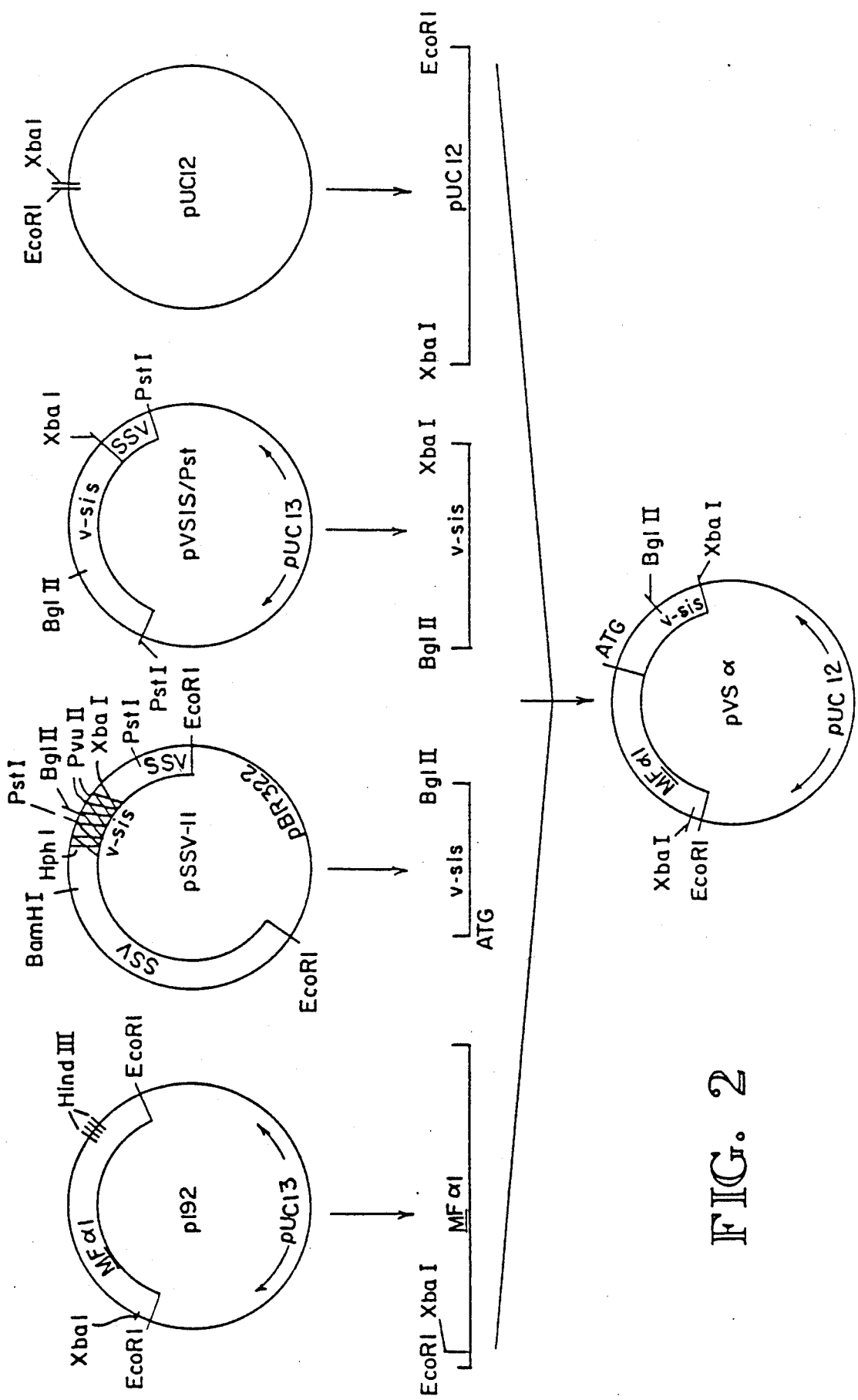
FIG. 2 illustrates the construction of a plasmid which contains the MFα1 promoter and secretory signal sequence upstream of the v-sis gene.

Prior to setting forth the invention, it may be helpful to an understanding thereof to set forth definitions of certain terms to be used hereinafter.

Polypeptide: A polymer of amino acids.

Reading Frame: The arrangement of nucleotide codons which encode an uninterrupted stretch of amino acids. During translation of an mRNA, the proper reading frame must be maintained. For example, the sequence GCUGGUUGUAAG may be translated into three reading frames or phases, depending on whether one starts with G, with C, or with U, and thus may yield three different peptide products. Translation of the template begins with an AUG codon, continues with codons for specific amino acids, and terminates with one of the translation termination codons.

Coding Sequence: DNA sequences which in the appropriate reading frame directly code for the amino acids of a protein.

Complementary DNA: or cDNA. A DNA molecule or sequence which has been enzymatically synthesized from the sequences present in an mRNA template.

Secretory Signal Sequence: That portion of a gene encoding a signal peptide. A signal peptide is the amino acid sequence in a secretory protein which signals its translocation into the secretory pathway of the cell. Signal peptides generally occur at the beginning (amino terminus) of the protein and are 20–40 amino acids long with a stretch of 9–10 hydrophobic amino acids in their center. Very often the signal sequence is proteolytically cleaved from the protein during the process of secretion.

Cell Surface Receptor: A protein molecule at the surface of a cell which specifically interacts with or binds a molecule approaching the cell's surface. Once the receptor has bound the cognate molecule, it effects specific changes in the physiology of the cell.

Mitogen: A molecule which stimulates cells to undergo mitosis. Mitosis is asexual somatic cell division leading to two daughter cells, each having the same number of chromosomes as the parent cell.

Transformation: The process of stably and hereditably altering the genotype of a recipient cell or microorganism by the introduction of purified DNA. This is typically detected by a change in the phenotype of the recipient organism.

Transcription: The process of producing mRNA template from a structural gene.

Expression: The process, starting with a structural gene, of producing its polypeptide, being a combination of transcription and translation. An expression vector is a plasmid derived construction designed to enable the expression of a gene carried on the vector.

Plasmid: An extrachromosomal double stranded DNA sequence comprising an intact "replicon" such that the plasmid is replicated in a host cell. When the plasmid is placed within a unicellular organism, the characteristics of that organism may be changed or transformed as a result of the expression of the DNA sequences of the plasmid. For example, a plasmid carrying the gene for tetracycline resistance (tet$^R$) transforms a cell previously sensitive to tetracycline into one which is resistant to it.

Yeast Promoter: DNA sequences upstream from a yeast gene which promotes its transcription.

Biological Activity: Some function or set of activities performed by a molecule in a biological context (i.e., in an organism or an in vitro facsimile). In the case of PDGF, these biological activities include binding to cell surface receptor molecules, inducing chemotaxis and inducing mitogenesis of responsive cell types.

As noted above, human platelet derived growth factor (PDGF) has been shown to be a major mitogenic protein in serum. PDGF is known to be composed of two polypeptide chains, an A chain and a B chain, which are held together by disulfide bonds to form the biologically active molecule. The A chain and B chain alone do not appear to exhibit any mitogenic activity, (Raines and Ross, ibid.) and attempts to reconstitute activity by reoxidation of the reduced polypeptides have not been successful. Recently, the amino acid sequence of the B chain has been shown to be substantially homologous to a portion of the v-sis gene product, p28$^{sis}$ (Doolittle et al., Science 221: 275, 1983; Waterfield et al., Nature 304: 35, 1984; and Johnson et al., Embo 3: 921, 1984). The homology between these two proteins strongly suggests that they are derived from the same or closely related cellular genes.

Given the fact that the B chain alone is not biologically active and that previous attempts directed toward expressing v-sis sequences in E. coli did not yield mitogenic material, it would not be expected that merely expressing a portion of the v-sis gene homologous to a portion of the PDGF gene in a microorganism would result in a molecule which exhibited mitogenic activity. The present invention however, unlike the previous attempts noted above, was designed to express the v-sis gene or portions thereof absent of heterologous sequences, such that the expressed molecules are more closely related to the B chain of PDGF. Further, the expression system of the present invention was designed to produce the gene product via a eucaryotic secretory pathway. This enables the expressed protein molecules to be properly processed and assembled such that they exhibit biological activity. Indeed, the present invention, in contrast to previous efforts, results in the secretion of PDGF analogs which are biologically active.

In its active form, PDGF is a heat stable protein composed of heterogeneously sized species of between 28,000 and 31,000 Daltons, all of the individual species being active in and stimulating DNA synthesis (Raines and Ross, ibid.; Deuel et al., J. Biol. Chem. 256: 8896, 1981; Antoniades, PNAS 78: 7314, 1981). Where individual species withmolecular weights of 27,000; 28,500; 29,000; and 31,000 Daltons have been isolated and assayed, they have been found to have comparable mitogenic activity and amino acid composition (Raines and Ross, ibid.) Further, these species show extensive tryptic peptide homology. The slight variations in size among the species are most probably due to differences in carbohydrate composition and proteolysis.

Through studies of PDGF which has been extensively purified from platelet-rich human plasma, it is likely, as noted above, that PDGF is composed of two polypeptide chains, an A chain (14,000 Daltons) and a B chain (16,000 Daltons), which are disulfide bonded together to form the biologically active dimer molecule (Raines & Ross, Deuel et al., Antoniades, ibid.). The PDGF nomenclature found in the literature is not consistent (Doolittle et al., Water-field et al., Raines and Ross, Johnson et al., ibid.). The nomenclature of Johnsson et al., ibid.) wherein the two polypeptides found in pure PDGF are called A chain and B chain. The B chain is homologous to p28$^{sis}$ and was previously called "peptide I" (Waterfield et al., ibid.) or "la" (Doolittle et al., ibid.). The A chain was previously termed "peptide II" (Waterfield et al., ibid.) or "2a" (Doolittle et al., ibid.). Data derived from a partial amino acid sequence of PDGF indicate that the two polypeptide chains (A chain and B chain) show some homology (Doolittle et al., ibid., Waterfield et al., ibid., and Johnsson et al., ibid., Antoniades and Hunkapiller, Science 220: 963, 1983). The A chain and B chain alone do not appear to exhibit any mitogenic activity, and attempts to reconstitute activity by reoxidation of the reduced polypeptides have not been successful (Raines & Ross, ibid.).

The v-sis gene, as mentioned above, is the transforming gene of simian sarcoma virus (SSV). The v-sis gene has been cloned and its DNA sequence determined (Devare et al., PNAS 79: 3179, 1982; Devare et al., PNAS 80: 731, 1983). Analysis of this sequence revealed an open reading frame which could encode a 28,000 Dalton protein, designated p28$^{sis}$. Subsequently, such a protein was identified in SSV infected cells (Niman, ibid.; Robbins, ibid.). The predicted amino acid sequence of the v-sis gene product, p28$^{sis,}$ was found to have a high degree of homology with the actual amino acid sequence of a portion of the B chain of PDGF (Johnsson, ibid.). The homology of the PDGF B chain to the v-sis gene product begins at amino acid 67 of p28$^{sis,}$ a serine, and continues for approximately 109 amino acids to a threonine residue at amino acid 175. The amino acid sequences preceding and following the B chain homologous region of p28$^{sis}$ are not homologous to either the A or B chains of mature PDGF (Johnsson, ibid.) In addition, PDGF and p28$^{sis}$ have been shown to be similar antigenically (Niman, ibid.; Robbins, ibid.). The v-sis gene product, p28$^{sis,}$ a protein of approximately 225 amino acids, appears to be proteolytically processed to a protein of approximately 20,000 Daltons (p20$^{sis}$) in SSV infected cells (Niman, ibid.; Robbins, ibid.). This 20,000 Dalton protein can be immunoprecipitated with antiserum against PDGF.

As noted above, previous attempts at expressing v-sis sequences in prokaryotes did not yield biologically active material. Further, the v-sis gene product p28$^{sis,}$ as well as PDGF itself, are secreted mammalian proteins. In order to achieve biologically active material, the present invention utilizes the secretory pathway of eucaryotic cells to express the v-sis gene and derivatives of the v-sis gene. Expression and secretion of the v-sis gene product from a eucaryotic cell enables processing and assembly which results in molecules with native and active conformation.

The secretory pathways of most eucaryotes are believed to be similar. In particular, mammalian cell and yeast cell secretory pathways are well characterized and are homologous. The presence of a secretory signal sequence on the expressed polypeptide is an important element in eucaryotes, due to its role in introducing the molecule into the secretory pathway, thereby leading to proper assembling and processing. Provided that appropriate transcriptional promoter and secretory signal sequences are utilized, generally any eucaryote could express and secrete the v-sis gene product in a biologically active form.

An easily manipulable and well characterized eucaryote is the yeast cell. For these reasons, yeast was chosen as a model example of an appropriate eucaryotic cell within the present invention. Accordingly, the v-sis gene and fragments thereof encoding the 109 amino acids with homology to the PDGF B chain were inserted into yeast extrachromosomal elements containing a yeast promoter capable of directing the expression of biologically active PDGF analogs. In accordance with the present invention, the yeast promoter is followed downstream by a fragment of the v-sis gene which encodes a protein having substantially the same structure and/or mitogenic activity as PDGF.

Genes which encode a protein having substantially the same structure and/or mitogenic activity as PDGF include the v-sis gene or a derivative of the v-sis gene of simian sarcoma virus (SSV) or portions thereof or the human cDNA gene for PDGF or portions thereof. Specifically, DNA sequences encoding polypeptides substantially homologous to the B chain of PDGF are preferred. The genes to be utilized in the extrachromosomal element may be isolated using standard recombinant DNA techniques.

The human PDGF cDNA gene may be isolated from a human cDNA library made from an appropriate source of messenger RNA by using the v-sis gene or a fragment thereof as a hybridization probe. A preferred source of mRNA is human umbilical vein endothelial cells. These cells can be cultured in vitro for short periods of time and are known to secrete PDGF into the culture medium (DiCorleto and BowenPope, *PNAS* 80: 1919, 1983). The identity of this cDNA gene as that encoding PDGF may be verified by DNA sequencing.

Promoters which may be utilized in yeast include the yeast alpha-factor (MFαl) promoter and the yeast triose phosphate isomerase (TPI) promoter. Promoters may also be obtained from other yeast genes, e.g., Alcohol Dehydrogenase 1 (ADH1), Alcohol Dehydrogenase 2 (ADH2).

The constructions described herein were designed such that the v-sis gene product would be secreted from the yeast cell into the media. This was accomplished through use of the secretion signal sequence of the yeast mating pheromone alpha-factor (Kurjan and Herskowitz, *Cell* 30: 933, 1982; Julius et al., *Cell* 36: 309, 1984; and Brake et al., *PNAS* 81: 4642, 1984) although other secretion signals may be used. To ensure the efficient transcription termination and polyadenylation of mRNA, a yeast terminator sequence, such as the triose phosphate isomerase terminator, was added. (Alber and Kawasaki, *J. Molec. Genet. Appl.* 1: 419, 1982.)

Once an appropriate DNA fragment containing the gene of interest is identified, it is ligated to an appropriate promoter and secretory signal fragment. Methods of ligation of DNA fragments have been amply described (Maniatis et al., *Molecular Cloning: A Laboratory Manual* Cold Spring Harbor Laboratory 1982) and are well within the skill of those of ordinary skill in the art to perform. After preparation of the v-sis expression constructions, the constructs are inserted into a yeast expression vector.

The replicating plasmid YEp13, containing an origin of replication and a selectable marker, the LEU2 gene, was used for the initial expression constructions. The use of the selectable marker LEU2 in yeast cells deficient in their ability to synthesize leucine allows for the positive selection of those cells containing the LEU2 plasmid by their ability to grow on minus leucine growth media. Although these constructions directed the expression of a product having some mitogenic activity, it is preferable to use an expression vector which is more stably maintained within the host cell in order to produce more mitogenic activity per culture.

Suitable yeast expression vectors in this regard are the plasmids pCPOT and pMPOT, which include the *Schizosaccharomyces pombe* gene encoding the glycolytic enzyme triose phosphate isomerase (POT1 gene). Inclusion of the POT1 gene ensures the stable maintenance of the plasmid in an appropriate host cell due to its ability to complement the corresponding gene deletion present within this host cell. In addition, the MFαl promoter was replaced by the *Saccaromyces cerevisiae* TPI promoter with the intention of further increasing transcription and expression.

After preparation of the DNA construct incorporating the TPI promoter, the alpha factor signal secretory signal sequences, the appropriate segment of the v-sis gene or the human cDNA gene for PDGF, and the TPI terminator in an appropriate vector, the construct is transformed into the yeast host with a TPI deletion. Procedures for transforming yeast are well known in the literature.

The transformed yeast cells may be selected for by growth on conventional complex medium containing glucose when the pCPOT vector is utilized. A conventional medium such as YEPD (20 grams glucose, 20 grams Bacto-peptone, 10 grams yeast extract per liter) may be used. Once selected, transformants containing the v-sis expression constructions are grown to stationary phase on conventional complex media, the cells removed, and the medium concentrated. Noting that authentic human PDGF is a highly cationic and hydrophobic protein (Raines and Ross ibid., Antoniades ibid., Deuel et al., 1981, ibid.), it was expected that the putative yeast product would possess similar characteristics, allowing it to be concentrated on a hydrophobic chromatography matrix such as C8-Sepharose (Pharmacia Fine Chemicals AB, Uppsala, Sweden).

Using a variety of assays, it is demonstrated that growth media from yeast cultures expressing the v-sis derivatives possess biological activities identical to authentic human PDGF.

Expression of biologically active v-sis derivatives in eucaryotic cells other than yeast can be achieved by a person skilled in the art by using the appropriate expression/regulatory signals. Transcriptional promoters capable of directing the expression of v-sis sequences are chosen for their ability to give efficient and/or regulated expression in the particular eucaryotic cell type. Signal sequences capable of directing the v-sis gene product into the cell's secretory pathway are chosen for their function in the appropriate cell type. Other useful regulatory signals, such as transcription termination signals, polyadenylation signals and transcriptional enhancer sequences, are also chosen for their function in the appropriate cell type, the selection of which would be apparent to an individual skilled in the art.

The techniques of cell culture have advanced considerably in the last several years as have the number and varieties of mammalian cells which will grow in culture. Central to these advances is a better understanding of the nutritional requirements (i.e., hormones and growth factors) of cultured cells (Barnes and Sato, *Cell* 22: 649, 1980). The types of cells able to grow in culture can be crudely classified in two groups: normal and transformed. So-called "normal" cells are generally not immortal in culture, they do not form tumors when injected into animals and they retain a normal diploid karyotype. Normal cells may also retain much of their differentiated character in culture. Within the category of normal cells are those which will only grow for a limited number of generations in culture, termed "cell strains" or "primary cultures." Some normal cell lines, while not meeting all the criteria of transformation, may grow indefinitely in culture. Transformed cells are immortalized for growth in culture, typically have lost their differentiated phenotype, and have acquired karyotypic aberrations. They may also be independent of anchorage for growth and induce tumors when injected into the appropriate host animal. Cells in any of these categories which grow in vitro and possess PDGF receptors will be responsive to the PDGF analogs of this invention in culture.

To summarize the examples which follow, EXAMPLE I demonstrates the construction of a v-sis subclone of pSSV-11 in the *E. coli* replicating plasmid pUC13, subsequently designated pVSIS/Pst. EXAMPLE II demonstrates the construction of the plasmid pVSα, which includes the ligation of v-sis to the MFol promoter and secretory signal sequence. EXAMPLE III demonstrates the oligonucleotide directed deletion mutagenesis of the first 195- base pairs of the v-sis gene using a technique which employs single stranded bacteriophage M13, in order to eliminate the first sixty-six amino acids of the v-sis gene product, p28$^{sis}$, which are not homologous to the B chain of PDGF. A resulting phage with the correct deletion was designated m11vsα. EXAMPLE IV demonstrates the construction of the plasmid pVSB. EXAMPLE V demonstrates the incorporation of the v-sis related constructions described in Examples II and III into the yeast replicating vector YEp13 and addition of yeast I PI terminator sequences. Subsequently, VS2α sequences were inserted into the plasmid pCPOT, which ensures the stable maintenance of the plasmid in the host cell. This plasmid was designated p117-2. EXAMPLE VI demonstrates the transformation of yeast host cells with the plasmids YEpVSo, YEpVS2α, p117-2 and control plasmids p270 and pCPOI, and subsequent transcriptional analysis. EXAMPLE VII demonstrates the concentration of the spent yeast growth media from cultures containing the v-sis expressing transformants and their subsequent analysis for PDGF-like material by the ELISA, radioreceptor and mitogenesis assays. Clear evidence is presented that these yeast media containing the v-sis related gene products described herein possess biological activities identical to authentic human PDGF.

The following examples are offered by way of illustration, and not by way of limitation.

EXAMPLES

Unless otherwise indicated, standard molecular biological methods were used. Restriction endonucleases and other DNA modification enzymes (i.e., T4 polynucleotide kinase, calf alkaline phosphatase, Klenow DNA polymerase) were obtained from Bethesda Research Laboratories, New England Biolabs, Boehringer-Mannhiem or Collaborative Research and were used as the manufacturer suggested unless indicated otherwise. M13 phage and pUC plasmid vectors and appropriate host strains were obtained from Bethesda Research Laboratories. *E. coli* cultures were transformed by the calcium chloride method of Dagert and Ehrlich (*Gene* 6: 23, 1979). Yeast cultures were transformed as described by Beggs (*Nature* 275: 104, 1978). Plasmid and M13 replicative form (RF) DNA were prepared from *E. coli* transformants by the method of Birnboim and Daly (*Nucleic Acids Research* 7: 1513, 1979). Single stranded M13 phage DNA was prepared as described by S. Anderson (*Nucleic Acids Research* 13: 3015, 1981). DNA fragments were extracted from agarose gels by the method of J. Langridge et al. (*Analyt. Biochem.* 103: 264, 1980). DNA sequencing was performed by the dideoxy method on M13 templates (Messing, *Meth. in Enzymology* 101: 20, 1983).

EXAMPLE I

Subcloning of V-SIS from pSSV-11

The SSV retroviral genome was cloned from SSV-11 nonproductively infected normal rat kidney (NRK) cells which had SSV integrated into their genome (Devare et al., 1982, ibid.). The SSV DNA was isolated as a 5.8 kilobase (kb) Eco RI fragment and subsequently inserted into the plasmid pBR322, resulting in the clone pSSV-11. This clone was obtained from S. Aaronson (National Institutes of Health, Bethesda, MD).

(FIG. 1A is a schematic restriction map of the 5.8 kilobase proviral genome of SSV. Only the restriction sites relevant to the present invention are indicated. The open box designates the p28$^{sis}$ coding portion of the v-sis gene.

FIG. 1B depicts the nucleotide sequence of the v-sis gene and some flanking SSV sequences. The v-sis gene is inserted 19 nucleotides 3' of the putative AIG initiation codon of the envelope (env) gene of SSV (Devare et al., 1982, ibid.). It is believed that transcription and translation of v-sis sequences are directed by SSV sequences resulting in an env-sis fusion protein. The nucleotide sequence shown in FIG. 1B is corrected from that published by Devare et al. in 1982 (ibid.). The corrections include those made by Devare et al. in 1983 (ibid.) and by the inventors herein. The original numbering scheme of Devare et al. (1982, ibid.) is retained here for ease of reference. The numbers assigned to the restriction sites in FIG. 1A are from FIG. 1B.

A subclone of pSSV-11 (FIG. 2) containing a portion of the v-sis gene was constructed in the *E. coli* replicating plasmid pUC13 (Vieira and Messing, *Gene*, 19: 259, 1982; and Messing, *Meth. in Enzymology* 101: 20, 1983). Five micrograms (ug) of pSSV-11 was digested with the restriction endonuclease Pst I and the 1.2 kb fragment containing sequences numbered 454-1679 (FIG. 1) was purified by agarose gel electrophoresis (0.9%) and extracted from the gel with cetyltrimethylammonium bromide (CTAB) plus butanol (Langridge et al., ibid.). Two ug of pUC13 was also digested with Pst I, phenol/chloroform (CHCl$_3$) extracted and ethanol (EtOH) precipitated. (orty ng of the 1.2 kb v-sis fragment and 50 ng of Pst I cut pUC13 were ligated overnight at room temperature with 40 units (u) of T$_4$ DNA ligase. The ligation mixture was used to transform *E. coli* K-12 strain JM83 (Messing, Recombinant DNA Technical Bulletin, NIH Publication No. 79-009, 2, No. 2, 43-48, 1979) in the presence of 5-bromo,4-chloro, 3-indolyl-B-D-galactoside (X-gal) and isopropyl B-D-thiogalactoside (IPIG). Plasmid DNA prepared from ampicillin resistant white colonies was digested with Pst I to verify the presence of the insert and the resulting plasmid was designated pVSIS/Pst.

EXAMPLE II

Construction of the Plasmid pVSα

A. Preparation of V-SIS for Fusion to MFα1.

Six hundred ug of plasmid pSSV-11 (FIG. 2) was digested with restriction endonucleases Bam HI and Pvu II in 200 microliters (ul) of 50 mM NaCl, 10 mM $MgC_{12}$, 10 mM Tris pH 7.5 (medium salt buffer), and 100 ug/ml bovine serum albumin (BSA), overnight at 37° C. The digestion products were electrophoresed through a 1.1% agarose gel and the 1100 base pair (bp) Bam HI-Pvu II fragment (FIG. 2) cut out, extracted and EtOH precipitated. The DNA pellet was dissolved in 75 ul Hph I buffer to which was added 20 ul of 1 mg/ml BSA and 5 ul Hph I. After overnight digestion at 37° C the mixture was electrophoresed through a 1.25% agarose gel and the 396 bp Hph I-Pvu II fragment isolated from the gel and EtOH precipitated. The DNA pellet was dissolved in 30 ul of Klenow buffer (6mM I is pH 7.5, 6 mM $MgCl_2$, 60 mM NaCl) and the 3' overhanging nucleotide at the Hph I cleavage site removed by treatment with 5 u of Klenow polymerase for 5 minutes at 37° C. One ul of a mixture containing all four deoxyribonucleotides each at 1 mM was added and the reaction mixture incubated an additional 10 minutes After phenol/$CHCl_3$/ether ($Et_2O$) extraction and EtOH precipitation, the DNA pellet was dissolved in 30 ul of medium salt buffer and digested with 5 u of Bgl 11 for three hours at 37° C. The DNA was electrophoresed through a 1.25% agarose gel and the 269 bp Hph I - Bgl II fragment extracted and EtOH precipitated. The Hph I cleavage terminus of this Klenow blunted fragment begins with the tri-nucleotide sequence

5'ATG...(FIG. 2)
3'TAC...

B. MFα1 Promoter and Secretory Leader Fragment

Figure 3:
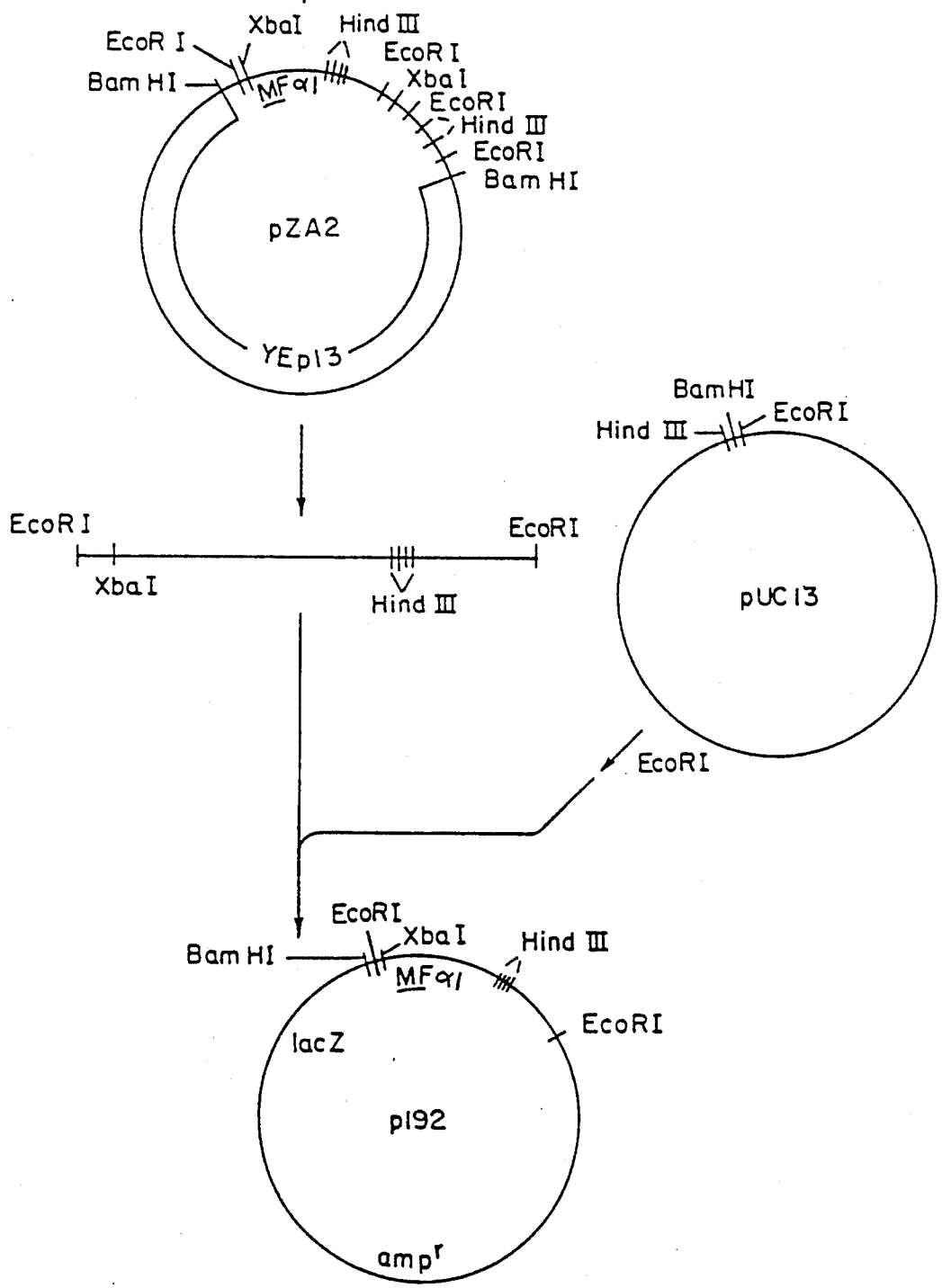
FIG. 3 illustrates the construction of plasmid p192.

Plasmid p192 (FIG. 3) comprises a portion of the gene for the yeast mating pheromone α-factor (MFα1 gene) cloned in the bacterial plasmid pUC13 (Vieira and Messing, ibid.; and Messing, Meth. in Enzymology 101: 20, 1983). Cloning of the MFα1 gene from a genomic library has been described by Kurjan and Herskowitz (ibid.). The gene was isolated in this laboratory in a similar manner, using as starting material a yeast genomic library of partial Sau 3A fragments cloned into the Bam HI site of Yep13 (Nasmyth and Tatchell, Cell 19: 753, 1980). From this library, a plasmid was isolated which expressed -factor in a diploid strain of yeast homozygous for the mat α2-34 mutuation (Manney et al., J. Cell Biol 96: 1592, 1983). The clone contained an insert overlapping with the MFα1 gene characterized by Kurjan and Herskowitz (ibid.). This plasmid, known as pZA2 (FIG. 3), was cut with Eco RI and the 1700 bp fragment comprising the MFα1 gene was purified. This fragment was then subcloned into the Eco Rl site of pUC13 to produce the plasmid p192.

Fifteen ug of plasmid p192 was digested in 30 ul of medium salt buffer with 20 units of Hind III overnight at 37° C. The reaction mixture was diluted to 60 ul with Klenow buffer and the four deoxyribonucleotides added to a final concentration of 50 uM each. Ten units of Klenow polymerase were added to the ice-cold mixture and incubation allowed to proceed 12 minutes at 15° C. Following phenol/$ChCl_3$/$Et_2O$ extraction, the aqueous phase was concentrated by lyophilization to a volume of 10 ul and digested with 20 units of Eco RI for 70 minutes at 37° C. The products were electrophoresed through a 0.9% agarose gel and the 1.2 kb Eco RI-Hind III (blunted) MFα1 fragment extracted and EtOH precipitated. This DNA fragment contains the transciptional promoter and secretory signal sequences of MFα1.

C. Preparation of v-sis 3' Sequences and Cloning Vector pUC12; Fragment Ligation Twenty ug of plasmid pVSIS/Pst was digested with Bgl II and Xba I in 40 ul of medium salt buffer. Subsequent electrophoresis through 1% agarose, extraction of the DNA and EtOH precipitation provided the purified v-sis 756 bp Bgl II-Xba I fragment (FIG. 2). E. coli replicating plasmid pUC12 (5 ug) was digested with Eco R! and Xba I and gel purified as above (FIG. 2).

Referring to FIG. 2, equimolar amounts of the four DNA fragments described above, adjusted to 10 ng of the 296 bp Hph !-Bgl II v-sis fragment, were mixed in 15 ul of ligase buffer (6 mM lris pH 7.6, 6 mM $MgCl_2$, 0.4 mM ATP, 2 mM spermidine, 20 mM DTT, and 100 ug/ml BSA) and ligated with 40 units of $T_4$ DNA ligase overnight ar 14° C. The reaction mixture was brought to room temperature, an additional 150 units of T4 ligase added, and incubated 10 more hours. Seven ul of the ligation mix was used to transform E. coli K-12 RRl (ATCC #31343; Bolivar E. et al., Gene 2: 95, 1977), and ampicillin resistant transformants selected. Plasmid DNA was prepared from 12 such bacterial colonies and digested with Xba 1. Two clones gave a~2.2 kb band predicted by the proper fragment alignment (FIG. 2). Further analysis of these by Bgl II-Xba I restriction mapping gave expected bands of approximately 1.5 kb from the MFα1/v-sis fusion and 760bp for the Bgl II-Xba I v-sis fragment. DNA sequence analysis verified the desired nucleotide sequence at the MFα1/v-sis junction. The resultant plasmid was designated pVSα.

EXAMPLE III

Oligonucleotide Directed Deletion

Mutagenesis of 66 Amino Terminal
v-sis codons

Homology between the v-sis protein $p28^{sis}$, and PDGF begins at amino acid 67 of $p28^{sis}$, a serine residue corresponding to the NH2 terminal residue of the PDGF B chain (Johnsson, ibid.)

Proteolytic processing of the MFα1 primary translation product occurs at the Lys-Arg cleavage signal 85 amino acids from the initiator methionine (Kurjan and Herskowitz, ibid.). A v-sis derivative was constructed in which the first 66 codons of p28sis were removed such that serine residue 67 of v-sis immediately follows the MF 1 Lys-Arg processing signal.

Figure 4:
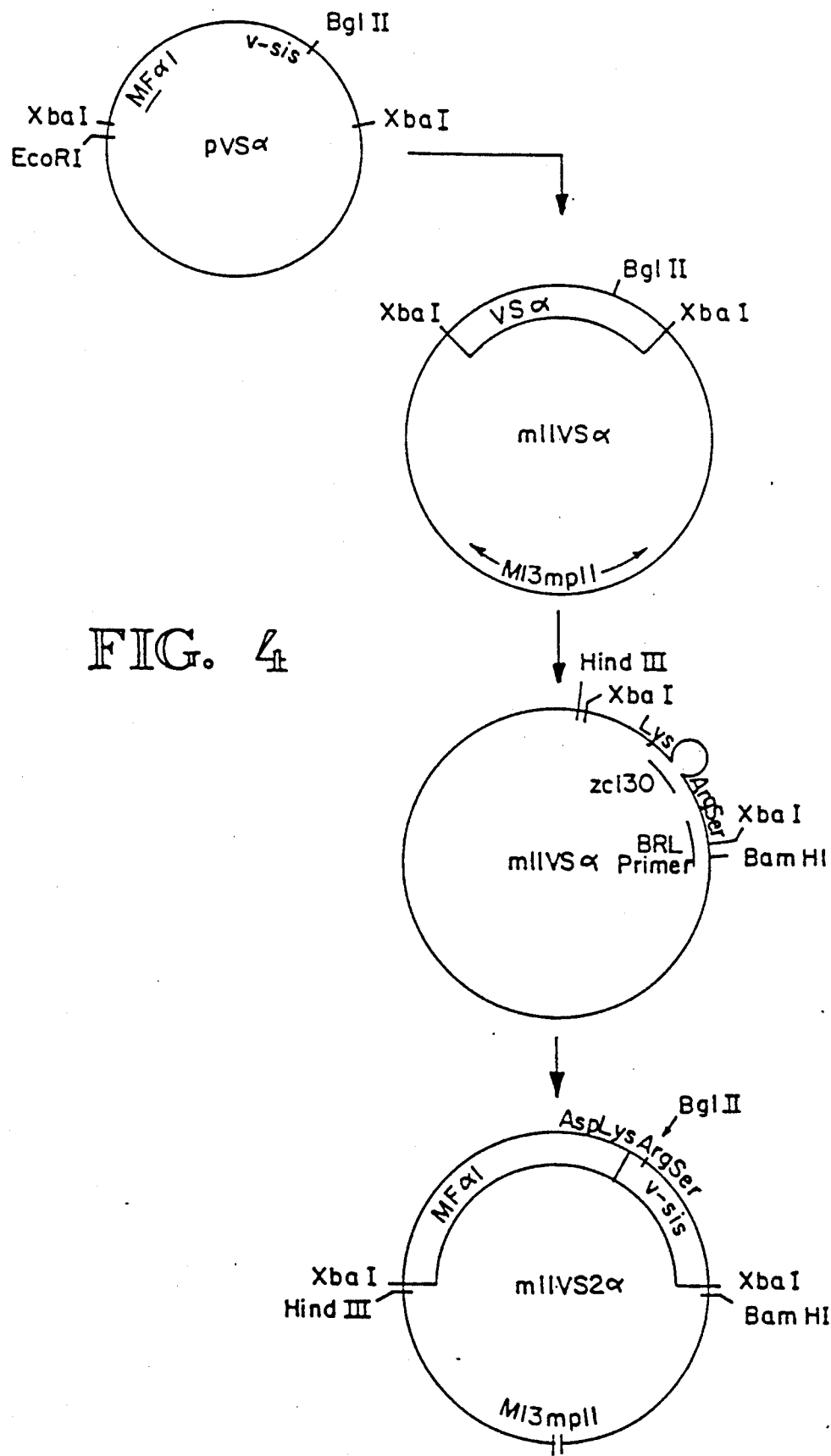
FIG. 4 illustrates the oligonucleotide directed deletion mutagenesis of the amino terminal sixty-six v-sis codons.

Referring to FIG. 4, approximately 40 ng of the gel purified 2.2 kb Xba I fragment of pVSα was ligated with 120 ng of Xba 1 digested, alkaline phosphatase treated M13mpll DNA (Messing, Meth. in Enzymology, ibid.). The ligation mixture was used to transform E. coli K-12 strain JM101 (ATCC 33876) in the presence of X-gal and IPTG. Isolated white plaques were picked and used to infect 3 ml cultures of log phase growth JM101 cells. Replicative Form (RF) DNA was prepared and clones identified which carried the insert fragment in the same orientation as the positive (+) strand form of the single stranded mature phage. Single-stranded phage DNA was prepared from one such clone and designated mIIVSα.

To precisely remove codons 1–66 of v-sis, oligonu-directed mutagenesis was performed essentially according to the two primer method of Zoller (Zoller, et al., *Manual for Advanced Techniques in Molecular Cloninq Course*, Cold Spring Harbor Laboratory, 1983). Oligonucleotide ZC 130 3' AGAAACCTATTTCCTC-GGACCCA 5' was synthesized on an Applied Biosystems 380-A DNA synthesizer. Fifty pmoles of ZC 130 were kinased in 10 ul of kinase buffer (BRL) with 4 units of T4 polynucleotide kinase for 45 minutes ar 37° C. The enzyme was inactivated by heating at 65° C for 10 minutes.

One-half pmole of mIIVSo was annealed with 1 pmole of kinased ZC 130 and 1.5 pmoles of universal sequencing primer (BRL) using conditions described (Zoller, ibid.), except that the annealing mixture was first heated to 65° C for 10 minutes, shifted to 37° C for 10 minutes, and then quickly chilled on ice. The annealed mixture was then treated with Klenow polymerase as described by Zoller (ibid.) to create circular duplex DNA. Portions of the elongation mixture were used to transform *E. coli* K12 JM 101 cells. The resulting phage plaques were screened for the proper deletion by transfer onto nitrocellulose filters and subsequent hybridization with $^{32}P$ phosphorylated ZC 130 at 65° C. Correctly juxtaposed sequences formed stable duplexes with the radioactive probe at the stringent hybridization temperature employed. Approximately 1% of the transformants screened gave positive signals by autoradiography. Ten clones were plaque-purified and RF DNA was prepared for restriction enzyme analysis. Five isolates showed the expected decrease in size of 195 bp to the 1450 bp Hind III-Bgl II fragment (FIG. 4). DNA sequence analysis of two isolates confirmed the correct fusion junction had been made, thus maintaining the proper translational reading frame. One of these phage was designated mIIVS2o.

EXAMPLE IV

Construction of the Plasmid pVSB

Because the product encoded by pVS2α is larger than authentic human PDGF B chain and because a smaller product might result in higher expression levels in a transformed yeast host cell, a vector was constructed comprising the v-sis sequence of pVS2α truncated at the 3' end. The polypeptide encoded by this sequence comprises 67 to 175 of p28sis and is homologous to the B amino acids 67 to 175 of p28$^{sis}$ and is homologous to the B chain of PDGF.

An expression vector containing this "B chain" sequence was constructed by combining elements of the pVS2 expression unit with a partial v-sis gene and a synthetic double-stranded DNA fragment encoding amino acids 158 to 175 of p28$^{sis}$. This synthetic fragment was designed to substitute preferred yeast codons for many of the 13 v-sis codons it replaces, and to supply a stop codon at the end of the coding sequence. The construction of this vector is illlustrated in FIGS. 8 and 9.

Plasmid YEpVS21α was digested with Pst I and Bam HI and the 1.8 kb fragment comprising the partial MFα1, v-sis, and TPI terminator sequences was purified by agarose gel electrophoresis. Plasmid pIC19R (obtainable from Dr. J. Lawrence Marsh, University of California, Irvine), comprising the polylinker shown in Chart 1 inserted into the Hind III site of pUC19 (Norrander et al., *Gene* 26: 101–106, 1983), was digested with Pst I and Bam HI, and the vector fragment was gel purified and joined to the 1.8 kb fragment from pVS2 to produce plasmid pVS2 T.

CHART 1

GAATTCATCGATATCTAGATCTCGAGCTCGCGAAAGCTT
Eco   R1   Eco   RV   Bgl   II   Sac   I   Hind III
      Cla I         Xba I      Xho I   Nru I Plasmid pM220 was digested with Bgl II and Psr I, and the ca. 1 kb fragment comprising the IPI promoter and the 5' portion of the MFα1 sequence was isolated and cloned in Bgl II +Pst I digested pIC19R. The resultant plasmid was digested with Cla I and Pst 1, and the TPI promoter - MFα1 fragment was gel purified. Plasmid pVS2 T was then cut with Cla I and Pst I and joined to the TPI promoter - Mfα1 fragment. The correct construct was identified by the presence of a 2.6 kb Cla I - Bam H1 fragment and was designated pTVS2αT.

Ten ug of plasmid pVSo was digested with Xma I and Sph I to completion. The resulting ca. 4.9 kb vector fragment, which also comprises most of the v-sis sequence, was purified by agarose gel electrophoresis, extraction of the DNA and EtOH precipitation.

In order to supply a new 3' terminus for the v-sis sequence, a double-stranded DNA fragment was constructed from oligonucleotides synthesized on an Applied Biosystems Model 380-A DNA synthesizer. 0.7 pmole of oligonucleotide ZC299 (Table 1) was heated with an equimolar amount of oligonucleotide ZC300 in a volume of 10 ul containing 40 mM NaCl for 5 minutes at 65° C.

TABLE 1

ZC299:  5'TAAG TGT GAA ATC GTT GCC GCG GCT
        AGA GCT GTT ACC TAA TCT AGA$^{3'}$

ZC300:  $^{3'}$GTACA TTC ACA CTT TAG CAA CGG CGC
        CGA TCT CGA CAA TGG ATT AGA TCT GGCC$^{5'}$

The mixture incubated at 37° C for 5 minutes and allowed to cool to room temperature. 0.2 pmole of the purified 4.9 kb vector fragment was added, the mixture ligated for 18 hours at 12° C. and used to transform *E. coli* HB101 (ATCC 33694) to Ampicillin resistance. DNA was prepared from Ampicillin-resistant colonies and digested with Bgl II and Xba I. After electrophoresis through agarose, the desired clone (known as pVSαB) was identified by loss of a ca. 750 bp Bgl II--Xba fragment and appearance of two smaller fragments of approximately 500 and 260 bp.

Approximately 8 ug of plasmid pTVS2αT was digested to completion with Xba I in a volume of 10 ul. The volume was increased to 40 ul with Bgl II buffer, and 6 units of Bgl II were added and the mixture was incubated at 37° C. Ten ul aliquots were removed to a stop buffer containing 50 mM EDTA at 15 and 30 minutes, and the remaining 20 ul stopped at 45 minutes. The resulting mixtures were separated by electrophoresis through 0.7% agarose. The ca. 4.6 kb Bgl II--Xba I vector fragment was cut out, extracted from the gel, and EtOH precipitated. Plasmid pVS B was digested with Bgl II and Xba I, and the ca. 260 bp fragment containing the synthetic 3' terminus and stop codon was isolated by electrophoresis through agarose, subsequent extraction from the gel, and EtOH precipitation.

The 4.6 kb Bgl II-Xba I vector fragment from pTVS2 T and the 260 bp Bgl II--Xba I fragment from pVSaB were ligated in the presence of T4 DNA ligase for 7 hours at room temperature. The reaction mixture was used to transform E. coli HB101 to Ampicillin resistance. DNA was prepared from transformants and the presence of the desired insert was confirmed by screening for a 550 bp Pst I--Xba I band on an agarose gel. A plasmid having the correct configuration was designated pVSB.

EXAMPLE V

Yeast Expression Vectors

A. Construction of Plasmids YEpVS α and YEpVS2α

Yeast Replicating Vector YEp13 (Broach, et al., Gene 8: 121, 1979) was used as an expression vehicle for v-sis derived constructions described in Examples II and III. YEp13 is a multicopy extrachromosomal plasmid containing a 2 micron replication origin and the yeast LEU2 gene. This allows for selection of the plasmid in yeast strains possessing a defective chromosomal LEU2 gene when grown on synthetic medium lacking leucine. Addition of yeast terminator sequences to foreign genes expressed in yeast ensures efficient transcription termination and polyadenylation of mRNA. The v-sis expression units VS and VS2 were placed adjacent to the TPI terminator fragment which was previously cloned into YEp13 (below).

Figure 5:
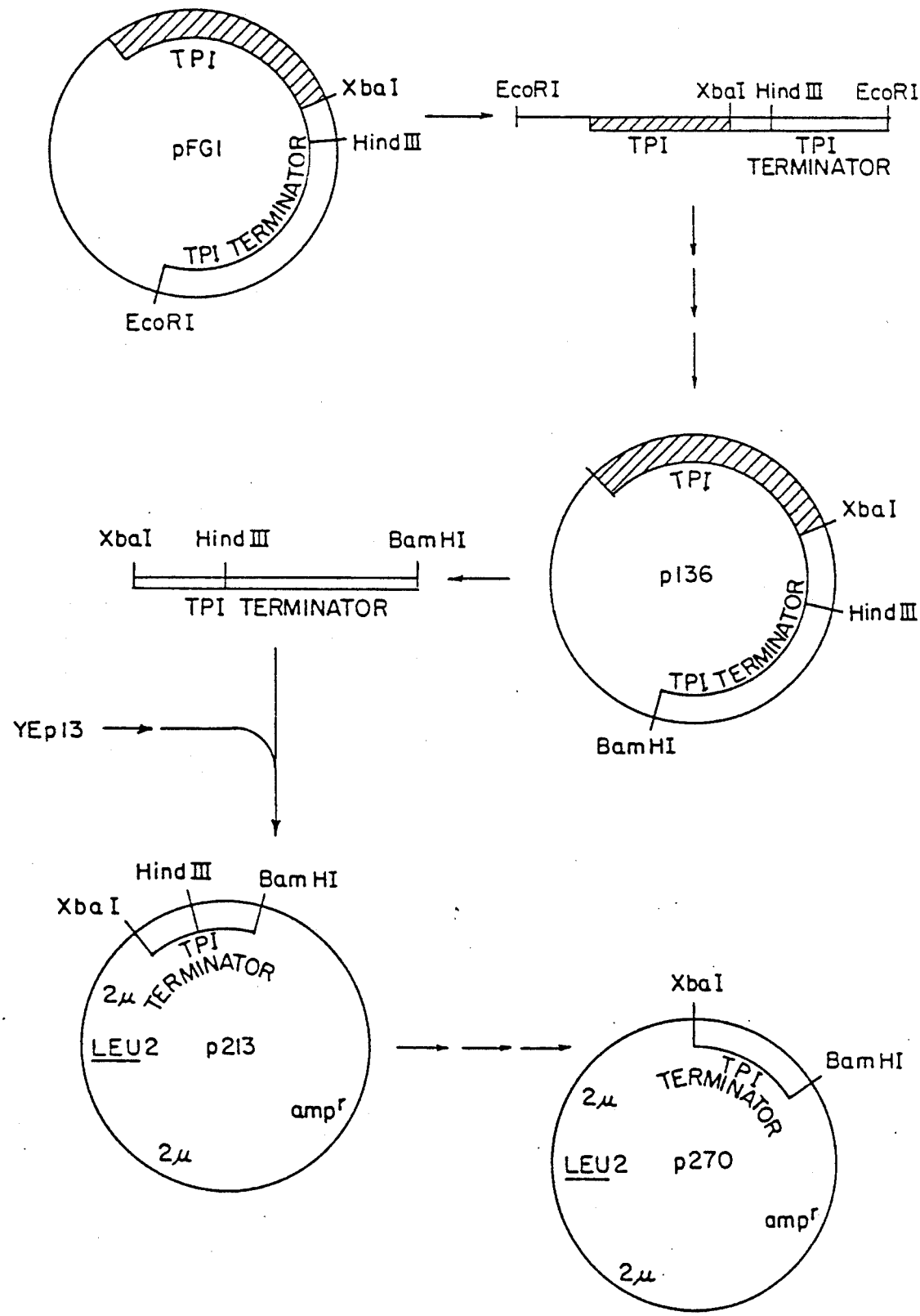
FIG. 5 illustrates the construction of plasmid p270.

Plasmid p270 (se e FIG. 5) contains the transcription terminator region of the yeast triose phosphate isomerase (TPI) gene. It was constructed in the following manner. The yeast TPI terminator fragment was obtained from plasmid pFG1 (Albert and Kawasaki, ibid.). It encompasses the region from the penultimate amino acid codon of the TPI gene to the Eco RI site approximately 700 base pairs downstream. A Bam HI site was substituted for this unique Eco RI site of pFG1 by first cutting the plasmid with Eco RI, then blunting the ends with DNA polymerase I (Klenow fragment), adding synthetic Bam HI linkers (CGGATCCA), and re-ligating to produce plasmid p136. The TPI terminator was then excised from p136 as a Xba I-Bam HI fragment. This fragment was ligated into YEp13 (Broach, et al., ibid.) which had bene linearized with Xba I and Bam HI. The resulting plasmid is known as p213. The Hind III site was then removed from the TPI terminator region of p213 by digesting the plasmid with Hind III, blunting the resultant termini with DNA polymerase I (Klenow fragment), and recircularizing the linear molecule using T4 DNA ligase. The resulting plasmid is p270.

Alternatively, p270 may be constructed by digesting plasmid pM220 (see below) with Xba I and Bam HI, purifying the TPI terminator fragment (~700bp) and inserting this fragment into XbaI and Bam HI digested YEp13.

Figure 6:
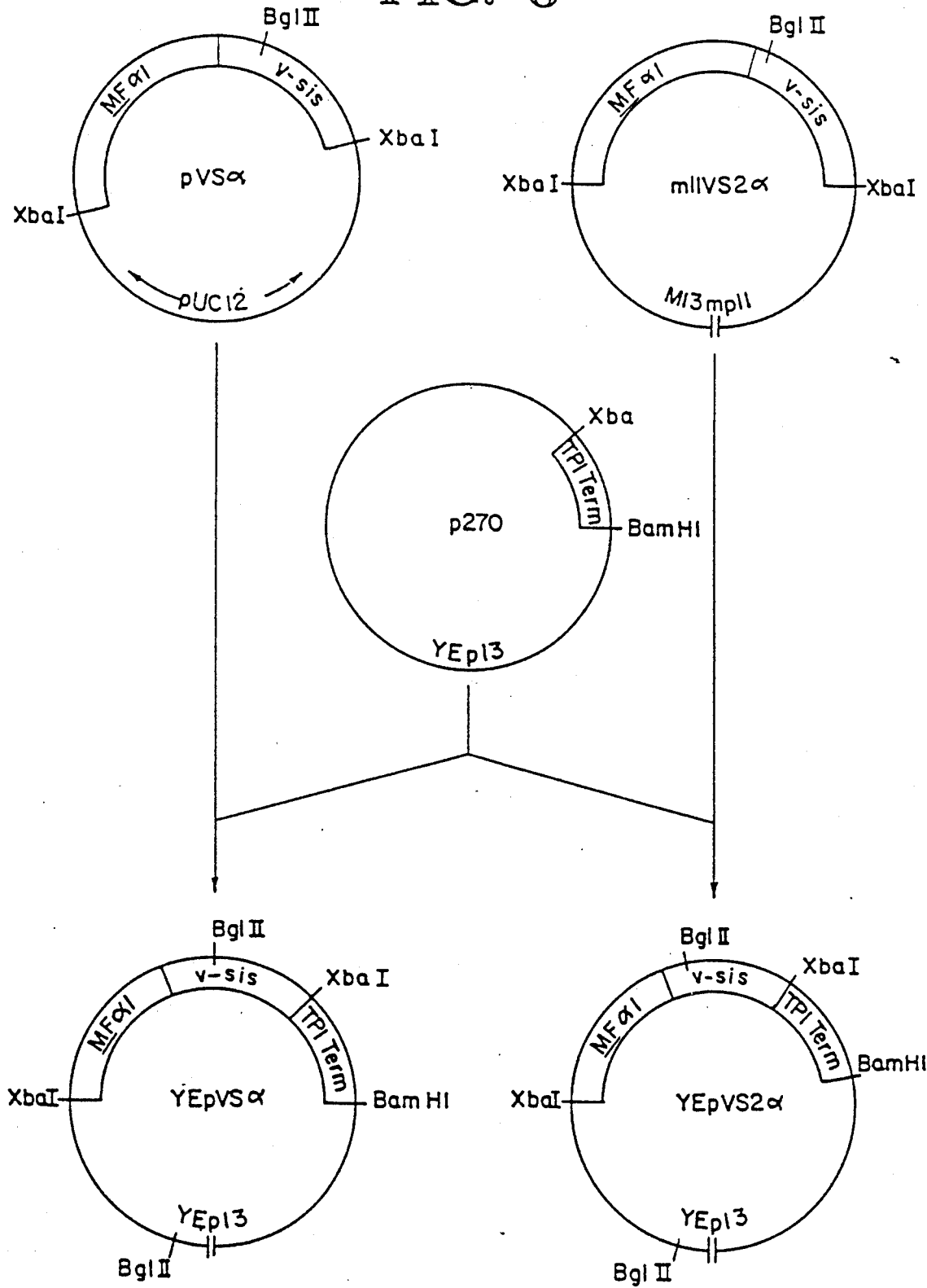
FIG. 6 illustrates the insertion of v-sis expression units upstream of the TPI terminator.

Referring to FIG. 6, plasmid p270 DNA was digested with Xba I and treated with calf alkaline phosphatase to prevent religation of the cohesive vector ends. V-sis expression units VSα and VS2α were prepared by Xba I digestion and agarose gel purification of pVSo and mIIvs2o, respectively. Each of the isolated fragments was ligated with an approximately equimolar amount of phosphatased p270 vector in the presence of 40 units of T4 DNA ligase and the ligation mixtures transformed into E. coli K-12 RR1. Plasmid DNA was prepared from ampicillin-resistant colonies and restriction enzyme analysis performed in order to identify clones which possessed the TPI terminator adjacent to 3' v-sis sequences. Presence of 3.3 kb or 3.1 kb Bgl II fragments after gel electrophoresis indicated the correct orientation of YEpVSαand YEpVS2α, respectively.

B. Insertion of VS2α Expression unit into pCPOT.

In order to achieve maximal protein production from a yeast culture, it is desirable to use expression vehicles which are very stably maintained in the host cell. Plasmid pCPOT is such a preferred expression vehicle.

E. coli HB101 transformed with pCPOT has been deposited with American Type Culture Collection under accession number 39685. Plasmid pCPOT comprises the 2 micron circle genome (Hartley and Donelson, Nature 286: 860, 1980), E. coli plasmid pBR322 replication and selection sequences, and the Schizosaccharomyces pombe DNA sequences encoding the glycolytic enzyme Triose Phosphate Isomerase (POT1). Presence of the POT1 tene in pCPOT ensures stable maintenance of the plasmid in the appropriate host background during growth on nonselective medium unwilling glucose as a carbon source.

The S. cerevisiae TPI promotor was used to control expression of VS2 sequences in pCPOT. Plasmid pM220 contains the TPI promoter fused to the MFα1 signal sequence. E. coli RRI transformed with pM220 has been deposited with American Type Culture Collection under accession number 39853.

Figure 7:
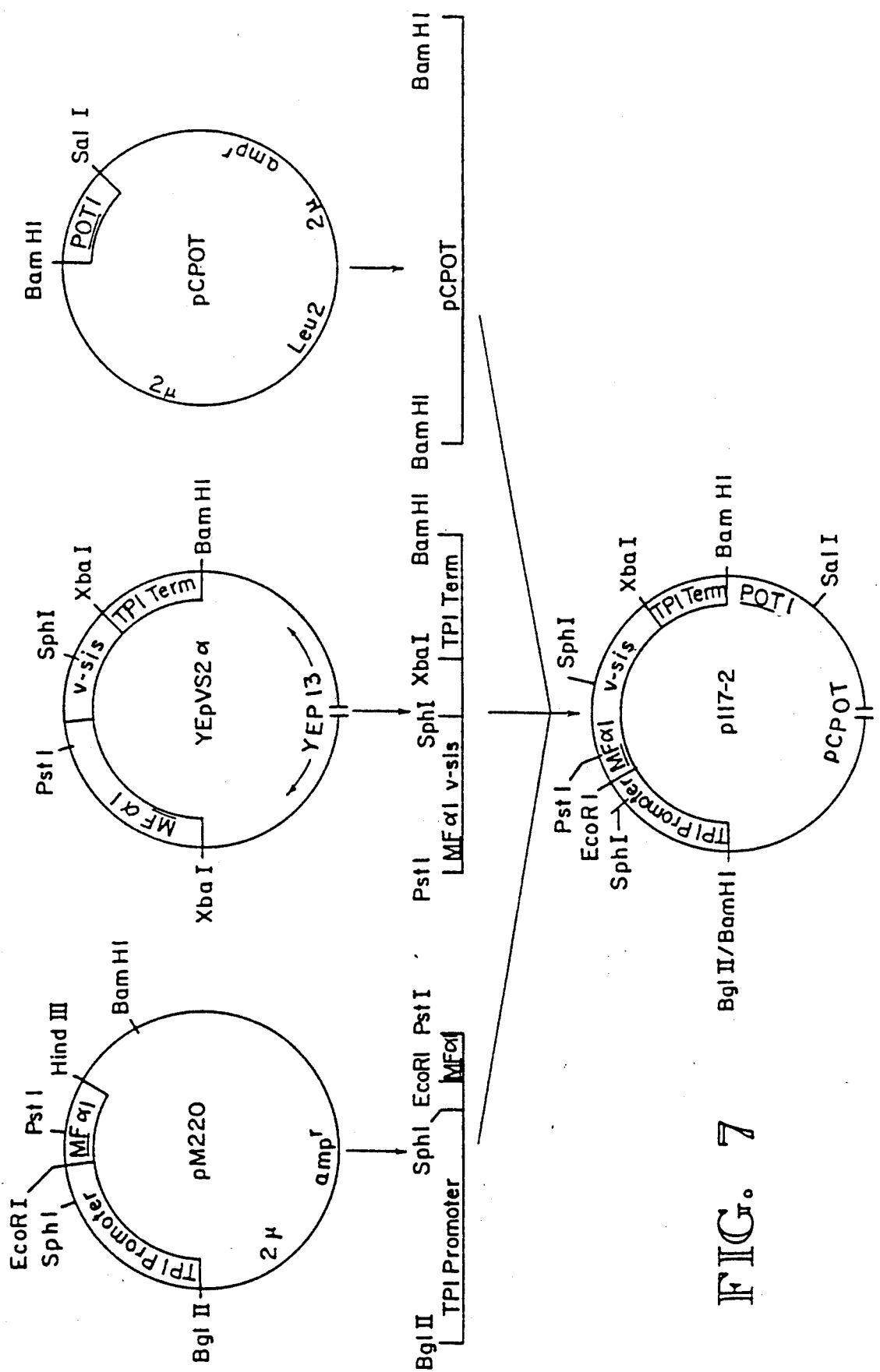
FIG. 7 illustrates the replacement of theαMF 1 promoter with the TPI promoter and inclusion of the VS2α construction in the pCPOT vector.

Referring to Figure 7, plasmid pM220 was digested with Bgl II and Bam HI, electrophoresed through a 0.9% agarose gel, and the 2.2 kb TPI promoter, MF 1 gene fragment extracted. The purified fragment was digested with Pst I and the resulting 1 kb Bgl II-Pst I fragment agarose gel-purified as above. Plasmid YEpVS2 was digested with Pst I and Bam HI, and the 1.8 kb MFα1/v-sis/TPI terminator fusion fragment gel-isolated. Plasmid pCPOT was digested with Bam HI, treated with calf alkaline phosphatase, phenol/CHCl3 was extracted, then purified by electrophoresis through agarose, extracted from the gel and EtOH precipitated.

Approximately equimolar amounts of the three isolated fragments described above (FIG. 7) were ligated overnight at 12° C and the ligation mixture used to transform E. coli K-12 strain DH1 (Hanahan, D. and Meselson, M., I. Mol. Biol. 166: 577, 1983) to ampicillin resistance. Plasmid DNA was prepared from transformants and restriction digest analysis used to ascertain the orientation of the insert fragments. Presence of the ~1500 bp Bam HI-Sal I ins fragment indicates that the Bam HI cohesive end of the TPI terminator fragment is oriented as shown in FIG. 7. The opposite orientation would create a Bam Hl/Bgl II fusion, not cleavable by Bam HI, and hence would not yield this fragment. The 800 bp Sph I fragment indicated that TPI promoter and v-sis fragments were properly fused at the Pst I site (FIG. 7). This plasmid was designated p117-2.

For expression of the v-sis derivatives in yeast, a stable expression vector comprising the REP1, REP2, REP3 and ori sequences from yeast 2 micron DNA and the *Schizosaccharomyces pombe* triose phosphate isomerase (POT1) gene was constructed. The POT1 gene provides for plasmid maintenance in a transformed yeast host grown in complex media if such host is defective for triose phosphate isomerase.

The POI1 gene was obtained from the plasmid pFAT-POT. *S. cerevisiae* strain E18 transformed with pFAT-POT has been deposited with ATCC under accession number 20699. The plasmid may be purified from the host cells by conventional techniques. The POT1 sequence was removed from pFATPOT by digestion of the plasmid with Sal I and Bam HI. This 1600 bp fragment was then ligated to pIC19R, which had first been linearized by digestion with Sal I and Bam HI. The Bam HI, Pst I and Sal I sites in the resultant plasmid were destroyed in two steps to produce plasmid pICPOT*. The Pst I and Sal I sites were removed by cutting with Pst I and Sal I; the ends were blunted by digesting the Pst I 3' overhang with DNA polymerase I (Klenow fragment) and filling in the Sal I 5' overhang with Klenow fragment. The blunt ends were then ligated. The Bam HI site was then removed by cutting the plasmid with Bam HI, filling in the ends with DNA polymerase I (Klenow fragment) and religating the blunt ends.

The 2u sequences were obtained from the plasmids YEp13 (Broach et al., *Gene* 8: 121-133, 1979) and C1/1. Cl/1 was constructed from pJDB248 (Beggs, *Nature* 275: 104-109, 1978) by removal of the pMB9 sequences by partial digestion with Eco RI and replacement by Eco RI-cut pBR322. The REP3 and ori sequences were removed from YEp13 by digestion with Pst I and Xba I and gel purification. REP2 was obtained from Cl/1 by digestion with Xba I and Sph I and gel purification. The two fragments were then joined to pUC18 (Norrander et al., *Gene* 26: 101-106, 1983) which had been linearized with Pst I and Sph I to produce plasmid pUCREP2,3. REP1 was obtained from Cl/1 by digestion with Eco RI and Xba I and gel purification of the 1704 bp fragment. The Eco RI--Xba I fragment was cloned into pUC13 which had been linearized with Eco RI and Xba I. The resultant plasmid was designated pUC13 +REP1. The pUC13 +REP1 plasmid was cut with Hind II and ligated in the presence of Eco RI linkers (obtained from Bethesda Research Laboratories). The REP1 gene was then removed as an Eco RI fragment of approximately 1720 bp. This Eco RI fragment was cloned into pIC7 (comprising the polylinker sequence shown in FIG. B inserted into the Hind III site of pUC8), which had been linearized with Eco RI and Xba I. The resultant plasmid was designated pICREP1#9.

To construct the final expression vector pMPOT2, pICPOT* was linearized by a partial Hind III digestion and complete Sst I digestion. Plasmid pUCREP2,3 was cut with Hind III and Sst I, and the fragment comprising REP2, REP3 and ori sequences was gel purified and joined to the linearized pICPOT*. The resultant plasmid, comprising REP2, REP3, ori, POI.1 and ampr sequences, was designated pMPOI1. REP1 was then removed from pICREP1 as a Bgl II--Nar I fragment and was ligated to pMPOT1, which had been cleaved with Bgl II and Nar 1. The product of this ligation was designated pMPOT2 (deposited with ATCC, accession number not yet assigned). Plasmid pMPOT2 was digested with Cla I and Bam HI, and the vector fragment was purified as above.

C. Insertion of v-sis Expression Units in pMPOT

1. Insertion of VSo expression unit into pMPOT2

Approximately 10 ug of plasmid pVS was digested with Bst EII to completion in a volume of 20 ul. Five units of Pst I were added, the mixture was incubated 30 minutes and the reaction stopped by the addition of EDIA. The quenched reaction mixture was immediately electrophoresed through a 1% agarose gel, and the ca. 800 bp partial Pst I--Bst EII band (comprising most of the MFα1 prepro sequence and the 5' portion of v-sis) was cut out, extracted from the gel, and EtOH precipitated.

Plasmid pTVS2αT was digested to completion with Pst I and Bst EII and purified by agarose gel electrophoresis. The resulting ca. 4.8 kb vector fragment and the 800 bp Pst I--Bst EII fragment were ligated in the presence of T4 DNA ligase for 6 hours at room temperature, and the ligation mixture was used to transform *E. coli* HB101 to ampicillin resistance. A plasmid was identified which contained a ca. 1450 bp Bgl II fragment, which indicated the presence of the insert. It was designated pTVSα.

Plasmid pTVS was digested to completion with Cla I and Bam HI, and the ca. 2.9 kb fragment containing VSo sequences was isolated by electrophoresis through agarose, extraction from the gel, and EtOH precipitation. The ca. 2.9 kb Cla I--Bam HI VSo fragment was ligated with Cla I and Bam HI digested pMPOT2 as described for pVS2 m (below). A plasmid containing a 2.9 kb Cla I--Bam HI insert was identified and designated pVSαm.

2. Insertion of VS2o expression unit into MPOT2.

Plasmid pTVS2αT was digested to completion with Cla I and Bam HI in Bam HI buffer. lhe buffer was adjusted to high salt (Maniatis et al, ibid.) and the DNA was digested to completion wit Pvu I, which cuts the vector sequences twice and permits resolution of the ca. 2.7 kb Cla I--Bam HI fragment containing the VS2 sequences on an agarose gel. This fragment was electrophoresed through 0.9% agarose, extracted, and EtOH precipitated. The fragment was then ligated with Cla I--Bam HI digested pMPOT2 in the presence of T4 DNA ligase for 20 hours at 13° C. The ligated DNA was used to transform *E. coli* HB 101 to ampicillin resistance, and plasmid DNA was prepared from the resulting colonies. A plasmid was identified which contained the 2.7 kb Cla I--Bam HI VS2 fragment and was designated pVS2αm.

3. Insertion of VSB expression unit into pMPOT2.

Plasmid pVSB was digested with Cla I and Bam HI, and the 2.2 kb fragment containing the "B chain" expression unit purified by agarose gel electrophoresis and EtOH precipitation. The fragments were ligated overnight at room temperature in the presence of T4 DNA ligase and the reaction mixture used to transform *E. coli* HB101 to ampicilreaction lin resistance. DNA was prepared from transformants and the presence of the insert verified by digestion with Cla I and Bam HI and agarose gel electrophoresis. The resulting expression vector was designated pVSBm.

EXAMPLE VI

Yeast Transformation; and

Analysis of v-sis Transcription

S. cerevisiae strain E8-11c (MAT αleu2-3, 112 pep 4-3; a haploid segregant of the cross E2-7B [ATCC 20689[x GK 100 [ATCC 20669]) was transformed with plasmids YEpVSα, YEpVS2α, p270, p117-2 and pCPOT. Transformants were selected and maintained in synthetic medium lacking leucine.

S. cerevisiae strain Ell-3c (ATCC Accession #20727) (MAT pep4-3 tpil) was transformed with plasmids pC POT and p117-2.transformants were selected and maintained in YEPD.

Figure 8:
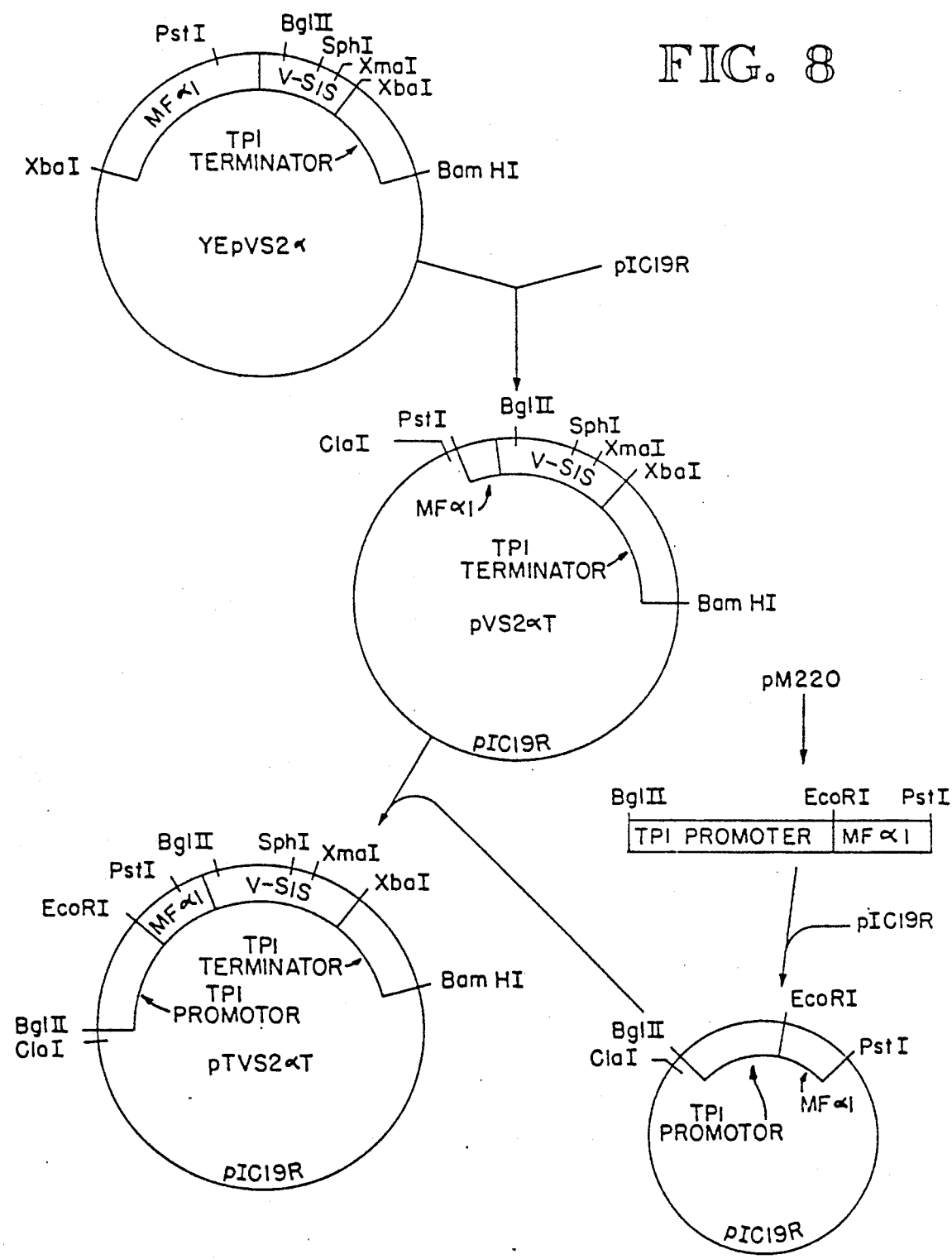
FIG. 8 illustrates the construction of plasmid pTVS2αT.
Figure 9:
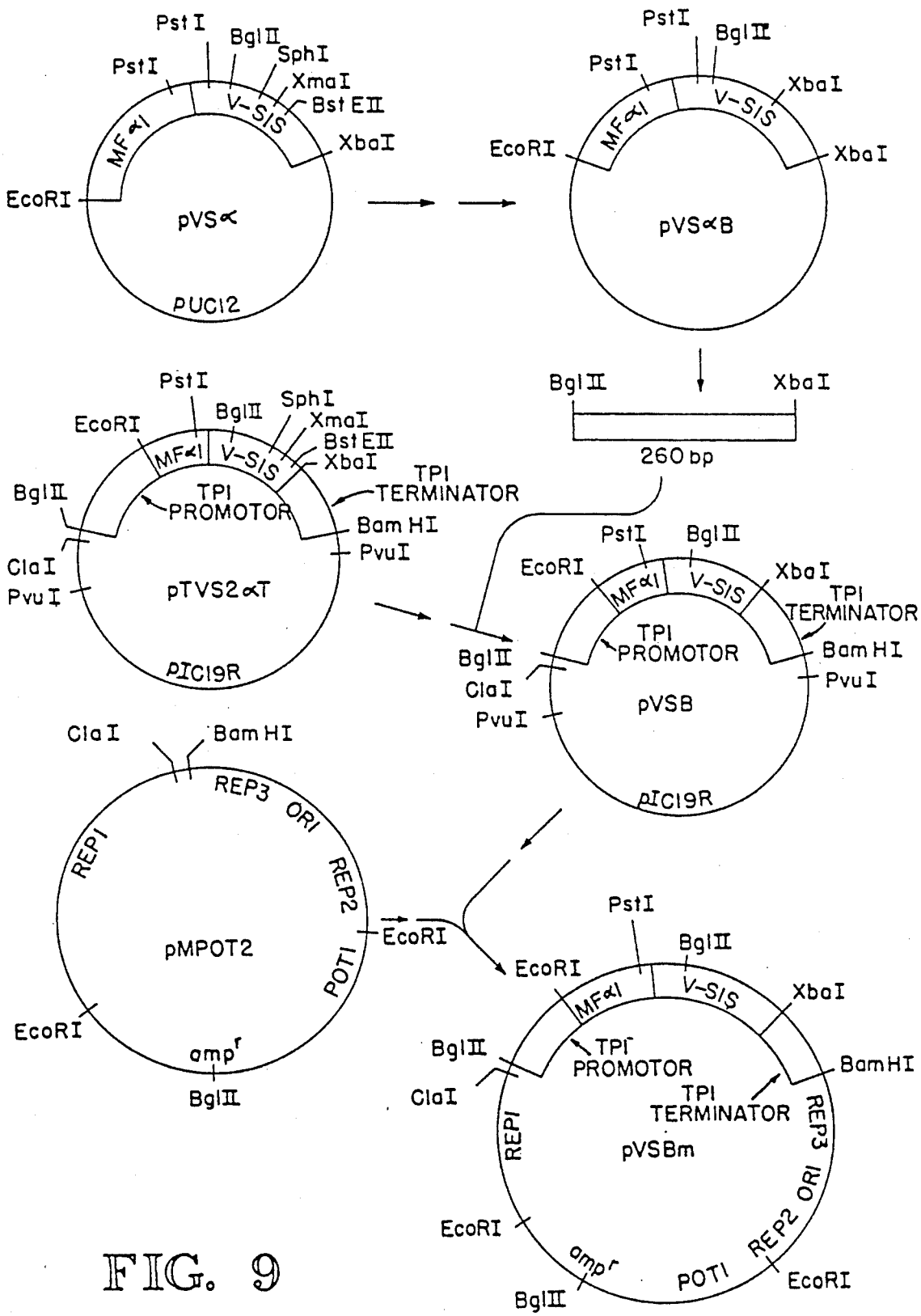
FIG. 9 illustrates the constuction of a B chain expression unit VSB and its introduction into the pMPOT vector.
Figure 10:
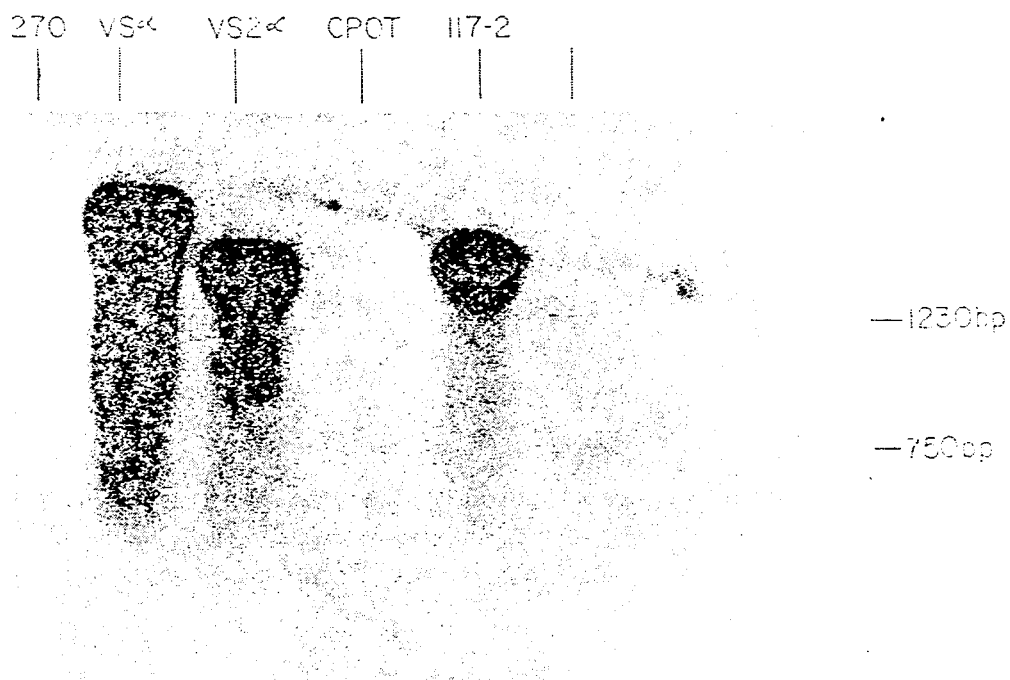
FIG. 10 depicts the electrophoretic and subsequent hybridization analysis of total RNA isolated from a yeast host transformed with various plasmids probed with a nick-translated v-sis gene fragment.

Referring to FIG. 8, presence of v-sis related mRNA transcripts was confirmed by electrophoretic and subsequent hybridization analysis of total RNA. Total RNA from the above described transformants in strain E8-11c was prepared by guanidinium thiocyanate extraction as described by Maniatis et al. (ibid.) with the following modifications: 100ml cultures were grown to a density of $1 \times 10^8$ cells/ml. The cells were pelleted by centrifugation and washed three times with $H_2O$, 2 mls of guanidinium lysis solution was added, followed by 0.5mm glass beads to just below the meniscus. The tubes were vortexed three times for 1 minute with cooling on ice between bursts. The solution was pipetted off and the RNA isolated by centrifugation through $CsCl_2$ as described (Maniatis et al., ibid.). Fifteen ug of RNA from plasmid transformants p270, YEpVSα, YEpVS2α;, pCPOI and p117-2 was glyoxylated, electrophoresed through a 0.9% agarose gel and transferred to nitrocellulose as described by Thomas (*PNAS* 77: 5201, 1980). The purified Pst I v-sis fragment from pVSIS/Pst was nick translated and hybridized to the filter bound RNA, and the hybridizing species detected by autoradiography (FIG. 10). Transcript bands of -1900 bp from YEpVSα, ~1650 bp from YEpVS2α, and ~1700 bp from p117-2 confirmed the transcription of the v-sis fusion constructs and the use of the transcription start and stop signals in the constructions. No v-sis related transcripts were detected in negative controls p270 and pCPOT.

Plasmids pVSαm, pVS2αm, pVSBm, and pMP012 were used to transform S. cerevisiae strain E18. Strain E18 is a diploid produced by crossing strains Ell-3c (ATCC No. 20727) and δtpi 29. δtpi 29 is produced by disrupting the triose phosphate isomerase gene of strain E2-76 (ATCC No. 20689), essentially as described by Rothstein (*Methods Enzymol* 101: 202-210, 1983).

EXAMPLE VII

Analysis of sis-related Products Expressed by Yeast; and

Biological Activity Assays

A. Concentration of Yeast Culture Medium.

Transformants carrying YEp13 and pCPOT derived v-sis constructions were grown in the appropriate media at 30° C (1.2 liter cultures) to stationary phase on a rotary air shaker with agitation at 220 rpm. Cultures were harvested, the cells removed by centrifugation, and the medium concentrated on a C-8 Sepharose (Pharmacia Fine Chemicals AB, Uppsala, Sweden) column which binds molecules of a hydrophobic nature. Authentic human PDGF is a highly cationic and hydrophobic protein (Heldin et al., *PNAS* 76: 3722, 1979; Raines and Ross, ibid.). The sis-related putative yeast product was expected to possess similar characteristics. The sis products expected hydrophobic character was exploited to concentrate it from the yeast media into which it was expected to be secreted. Molecules bound to the C-8 column are eluted from the matrix with suitable hydrophobic solvents.

Spent growth media from the transformed yeast cultures was adjusted to 5% EtOn and passed through an 8 ml C-8 Sepharose column at a flow rate of 2-3 ml per minute. The column was then washed with 100mls of 5% EtOH in 20 mM ammonium bicarbonate ($NH_4HCO_3$). The bound material was eluted with 20% propanol in 20mM $NH_4HCO_3$ and the eluate in 1-2 ml fractions. Fractions were assayed for protein content by light absorption at 280 nm, ($A_{280}$ of 1.4=1.0 mg protein/ml) or by the method of Lowry et al. (*J. Biol. Chem.* 193: 265, 1951). The concentrated fractions were combined, lyophilized, and then resuspended in 500-700 ul of PBS (phosphate buffered saline, pH 7.4).

Transformant p117-2 in strain Ell-3c grown under POT1 selection (with glucose as carbon source) was expected to produce significantly higher levels of PDGF-like material in the media and thus was analyzed after dialysis of the media against PBS without concentration.

Media samples from the transformants pVSαm, pVSα2m, pVSBm and pMPOT2 were concentrated by adsorption to CM-sephadex and elution with 1M NaCl in 1M acetic acid, pH 4.5. Il:e concentrated media were dialyzed against 0.1 M aceric acid, pH 7 and the amount of PDGF-like material in the concentrates was determined by ELISA.

B. Detection of PDGF-like Material By Enzyme-Linked Immunosorbent Assay (ELISA)

The expression of PDGF-like molecules by the yeast transformants was examined by ELISA and quantitated by comparison to a standard curve developed with purified human PDGF (Raines and Ross, ibid.). A typical standard curve was prepared as follows:

Purified human PDGF, 2.5 ng/ml in PBS, was incubated overnight with Immulon II (Dynatech Laboratories, Inc.) 96 well microtiter plates (100 ul/well) at 4° C. This coating solution was removed and 100 ul/well of 0.1% rabbit albumin in PBS was added and the plates incubated for 1 hour at 37° C. Samples of purified PDGF (0.1-40ng/ml) were separately incubated with goat anti-PDGF IgG (5 ug/ml) in PBS containing 0.05% Tween 20 and 1 mg/ml rabbit albumin (RSA). The microtiter plates were washed 5 times with 0.9% NaCl, 0.05% Tween 20, drained, and 100 ul of each test solution was added to the microtiter wells and incubated 2 hours at 37° C. The plates were washed as before, and peroxidaseconjugated swine anti-goat IgG (Tago, Inc.) diluted 1:1000 in PBS containing 0.05% Tween 20 and 1 mg/ml RSA was added for 2 hours at 37° C. The plates were washed as before and freshly prepared 04% o-phenylene diamine containing 0.012% hydrogen peroxide ($H_2O_2$) (100 ul/well) was added for 50 minutes at room temperature and the reaction stopped at 50 minutes by the addition of 4N $H_2SO_4$ (50 ul/well). Absorbance at 492 nm was determined using a Dynatech plate scanner. Each test point was measured in triplicate and plotted as the mean ± standard error. C-8 eluates of yeast culture media and unconcentrated media samples were diluted in PBS, assayed as described and compared to the PDGF standard curve.

Figure 11:
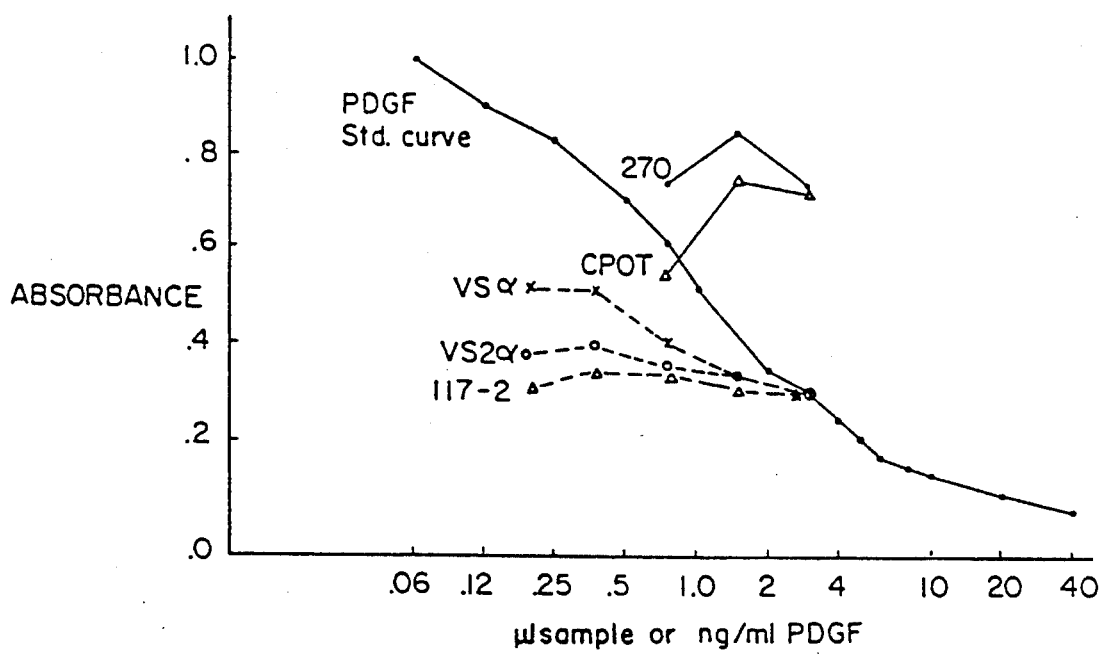
FIG. 11 depicts the results of ELISA of concentrated culture media from the yeast transformants containing plasmids pVSα, pVS2α, p117-2 and pCPOT.

Table 2 is a summary of assay results for a representative series of experiments. FIG. 11 depicts an ELISA of a range of C-8 eluate sample volumes measured, generating a dose-response curve which is compared to a standard curve from purified PDGF.

Figure 13:
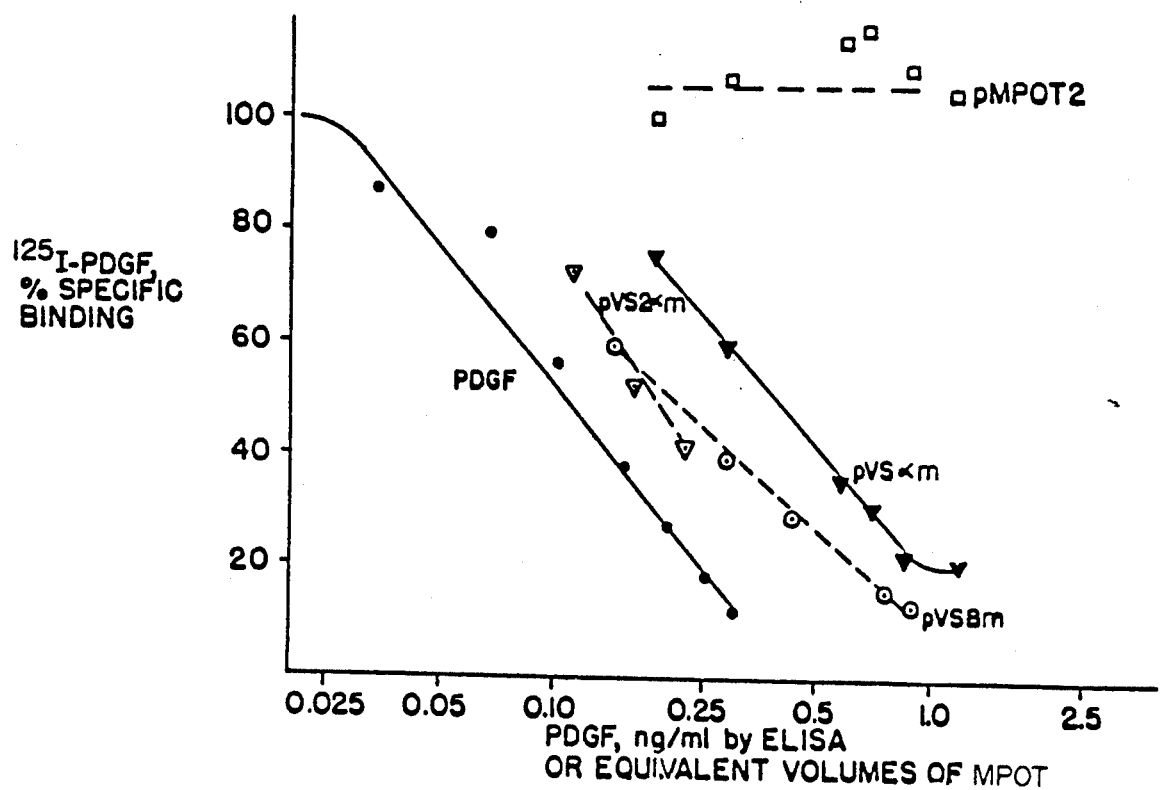
FIG. 13 is a dose response curve of PDGF receptor binding by media concentrates from yeast transformants containing plasmids pVSαm, PVS2αm, pVSBm and pMPOT2 compared to authentic PDGF.
Figure 14:
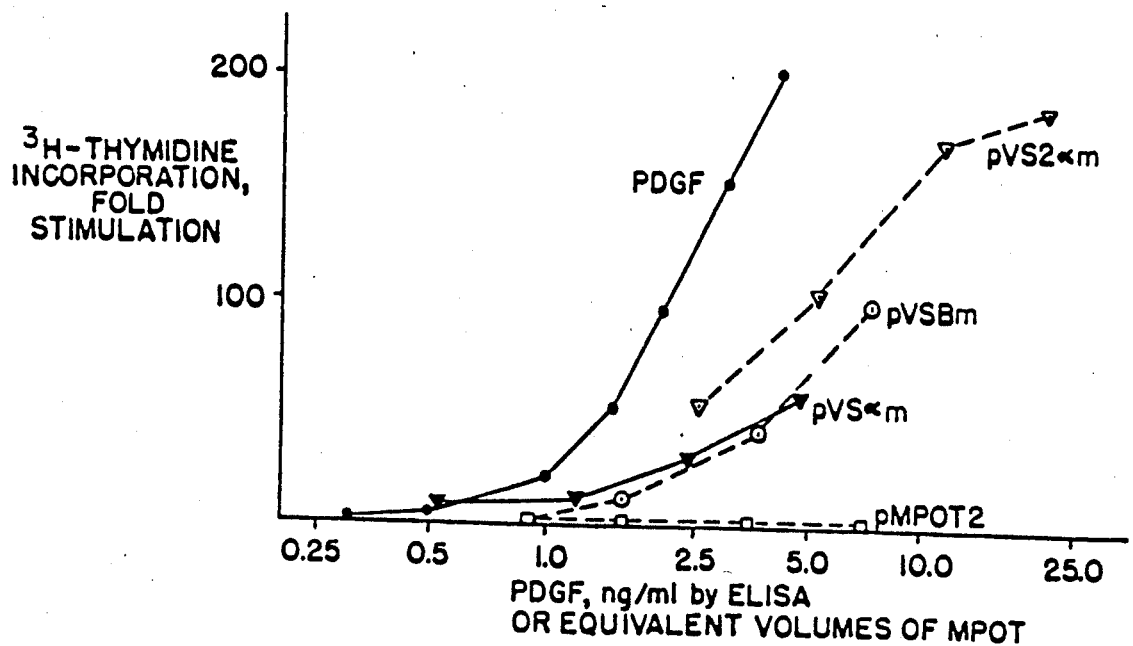
FIG. 14 is a dose response curve of mitogenic activity of media concentrates from yeast transformants containing plasmids pVSαm, pVS2αm, pVSBM, and pMPOT2 compared to authentic PDGF.

Raw ELISA data for the MPOT constructions is not shown, but has been incorporated into the radioreceptor and mitogenesis assay data as shown in FIGS. 13 and 14.

C. Radioreceptor Assay (RRA) for PDGF.

The radioreceptor assay for PDGF (Bowen-Pope and Ross, *J. Biol. Chem.* 257: 5161, 1982) is a specific and sensitive (0.2–2 ng/ml PDGF) method for detecting biologically active PDGF-like material in yeast. In this assay, PDG(-like material is tested for its ability to compete with purified, radio-labeled $125_I$ PDGF for binding sites on cell surface PDGF receptors. Results are interpreted by comparison to a standard curve generated with purified, unlabeled PDGF. Comparison of results obtained with other assay methods (e.g., ELISA) provides an indication of the strength of the receptor/ ligand interaction in addition to quantitation of the material bound. The assay is conducted as follows: Subconfluent monolayers of diploid human fibroblasts are prepared by plating $1.5 \times 10^4$ cells per $2cm^2$ culture well in Costar 24 well cluster trays in Dulbeccos Modified Eagles Medium (DMEM) supplemented with 1% human plasma-derived serum (PDS). Cultures are set on an ice tray and rinsed once with ice-cold binding rinse (Ham's medium F-12 buffered at pH 7.4 with 25mM HLP(S and supplemented with 0.25% BSA). One ml/well of test substance in binding medium is added and the cultures incubated in a refrigerated room on an oscillating platform for 3–4 hours. The trays are then placed on ice, aspirated, rinsed once with cold binding rinse and incubated for one hour as above with 1 ml/well binding medium containing 0.5 ng/ml $^{125}I$-PDGF. Labeling is terminated with 4 rinses of binding rinse and cell-associate d $^{125}I$-PDGF determined by extraction with solubilization buffer. Standard curves are obtained using 0, 0.05, 0.1, 0.2, 0.4, and 0.8 ng/ml purified PDGF and test samples compared to these values.

Results obtained by RRA for yeast C-8 eluates and IX media samples are given in Table 2.

In addition, PDGF receptor binding by CM-sephadex media concentrates from yeast transformants containing plasmids pVSam, pVS2am, pVSBm, and pMPOI2 was compared to authentic PDGF. The results were interpreted by comparison to a standard curve generated with purified, unlabeled PDGF, as shown in FIG. 13. Media from cultures transformed with the v-sis constructions are shown to compete with $^{125}I$-PDGF for binding to the PDGF receptor. Media from yeast cells transformed with pMPOI2 do not compete with radio-labeled PDGF for receptor binding.

D. Mitogenesis Assay

The ability of PDGF to stimulate DNA synthesis and cell growth in culture was the basis for its definition and discovery. $^3H$-Thymidine incorporation into DNA of cultured cells responsive to PDGF (Raines and Ross, *Meth. in Enz.* 109: in press) is a preferred method for demonstrating the biological activity of PDGF-like molecules produced in yeast.

Test samples in 10mM acetic acid (100 ul/well) are added to quiescent cultures of mouse 3T3 cells in $2cm^2$ Costar 24-well culture dishes ($2-3 \times 10^8$ cells/well in 1 ml). Quiescent test cultures can be obtained by plating the cells in 10% serum and allowing them to deplete the medium, 4–5 days. The test samples are removed from the wells at 24 hours and replaced with 0.5 ml of fresh medium per well containing 2 uCi/ml [$^3H$]-Thymidine and 5% (v/v) calf serum. After an additional 2-hour incubation at 37° C. the cells are harvested by: aspirating off the medium, washing the wells twice each with 1 ml of ice-cold 5% ICA; soublizing TCA-insoluble material in 0.8 ml 0.25N NaOH with mixing; and counting 0.6 ml of this solution in 5 ml Aquasol in a liquid scintillation counter. Fold stimulation over control wells (100 ul of 10mM acetic acid alone) is determined, (normally 30–50 fold maximal stimulation) and compared to a standard curve obtained using purified PDGF preparations.

Figure 12:
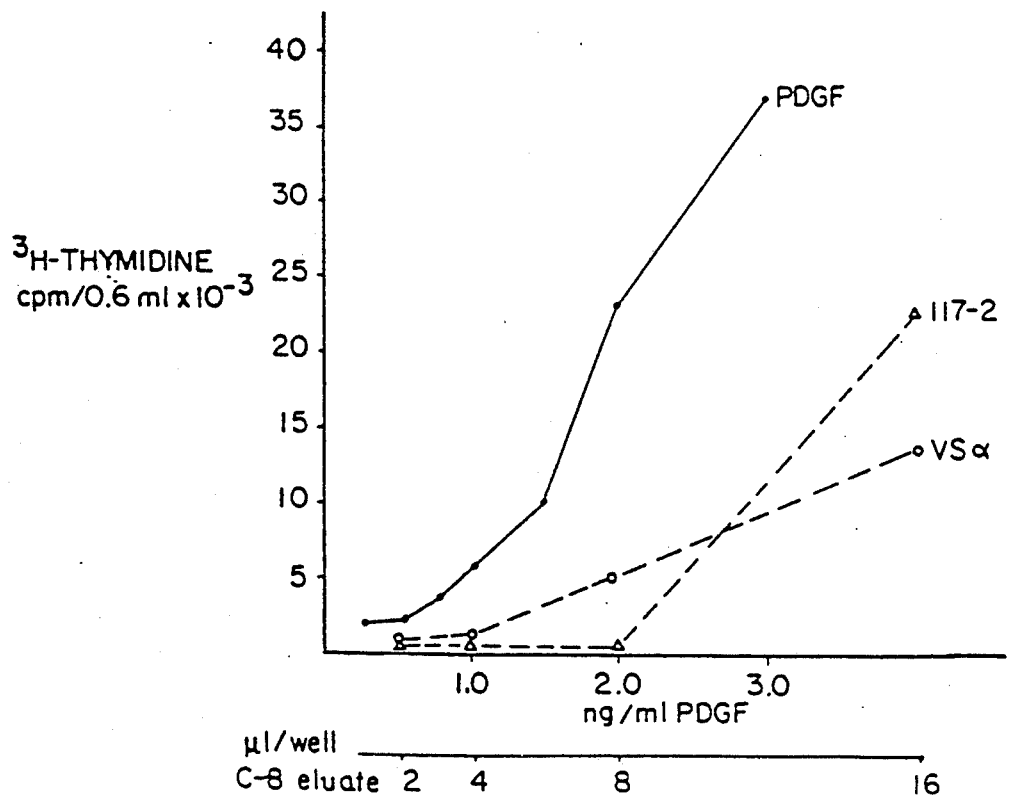
FIG. 12 is a dose response curve of mitogenic activity of concentrated culture media from yeast transformants containing plasmids pVSα and p117-2, compared to purified PDGF.

Table 2 presents results obtained in the mitogenesis assay for PDGF-like material produced in yeast and compares the activities of the PDGF-like material as measured by the above-described assay methods. FIG. 12 depicts the mitogenic response elicited by concentrated media from p117-2 transformed E11-3c and pVSα transformed E8-11c compared to that obtained with purified human PDGF.

TABLE 2

| Preparation | Transformant | ug/ml Protein | ng/ml PDGF by | | |
|---|---|---|---|---|---|
| | | | ELISA | RRA | MITOGENESIS |
| C-8 Eluates | | | | | |
| | pVS /E8-11c | 2.0 | 188 | 4.6 | 102 |
| | pVS2 /E8-11c | 16 | 864 | 16–97 | 310 |
| | p117-2/E11-3c | 1.44 | 120 | 13.9 | 87 |
| 1X Media | p117-2 E11-3c | — | 4.2 | 0.18 | 2.5 |

In addition, the mitogenic response elicited by CM-sephadex concentrates from yeast transformants containing plasmids pVSαm, pVS2αm, pVSBm, and pMPOT2 was compared to that obtained with authentic PDGF. Referring to FIG. 14, media from cultures transformed with the v-sis constructions stimulated uptake of $^3H$-thymidine by quiescent 3T3 cells. As noted above, uptake of $^3H$-thymidine by quiescent 3T3 cells is taken to be indicative of mitogenic stimulation. Media from yeast cells transformed with pMPOT2 showed no mitogenic activity.

The data presents clear evidence that growth media from the yeast strains constructed herein possess biological activities identical to authentic human PDGF. Further, these activities are readily detectable in nonconcentrated (1X) media from p117-2 transformed strain E11-3c grown under POT1 selection.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A protein homodimer consisting essentially of human PDGF B-chains, said protein being essentially free of the A-chain of PDGF.

2. The protein of claim 1 wherein said protein is essentially free of other proteins of mammalian or viral origin.

3. A protein consisting essentially of two disulfide bonded polypeptide chains, each of said chains consisting essentially of the amino acid sequence shown in FIG. 1B, beginning with serine, number 67, and ending with threonine, number 175, said protein being essentially free of other proteins of mammalian of viral origin.

4. A recombinant protein homodimer comprising component polypeptide chains substantially identical to the B-chain of human PDGF, said protein being essentially free of the A-chain of PDGF.

5. The protein of claim 4 wherein said protein is essentially free of other proteins of mammalian or viral origin.

6. A recombinant protein homodimer consisting essentially of component polypeptide chains substantially identical to the B-chain of human PDGF, said protein being essentially free of the A-chain of PDGF.

7. The protein of claim 6 wherein said protein is essentially free of other proteins of mammalian or viral origin.

* * * * *

UNITED STATES PATENT AND TRADEMARK OFFICE
CERTIFICATE OF CORRECTION

PATENT NO. : 5,045,633

DATED : September 3, 1991

INVENTOR(S) : Mark J. Murray; James D. Kelly

It is certified that error appears in the above-identified patent and that said Letters Patent is hereby corrected as shown below:

In column 23, claim 3, line 6, after "mammalian" please delete "of" and substitute therefor -- or --.

Signed and Sealed this

Ninth Day of February, 1993

Attest:

STEPHEN G. KUNIN

*Attesting Officer*    Acting Commissioner of Patents and Trademarks